(12) United States Patent
Kelly

(10) Patent No.: US 6,365,712 B1
(45) Date of Patent: Apr. 2, 2002

(54) METHODS AND COMPOSITIONS FOR INHIBITING INFLAMMATION AND ANGIOGENESIS COMPRISING A MAMMALIAN CD97 α SUBUNIT

(75) Inventor: Kathleen Kelly, North Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/284,819

(22) PCT Filed: Oct. 24, 1997

(86) PCT No.: PCT/US97/19772

§ 371 Date: Aug. 20, 1999

§ 102(e) Date: Aug. 20, 1999

(87) PCT Pub. No.: WO98/17796

PCT Pub. Date: Apr. 30, 1998

Related U.S. Application Data

(60) Provisional application No. 60/027,871, filed on Oct. 25, 1996.

(51) Int. Cl.⁷ ............ A61K 38/00; C07K 2/00; C07K 4/00; C07K 5/00; C07K 7/00
(52) U.S. Cl. ............ 530/300; 530/324; 530/350; 530/380; 530/385; 530/386; 530/387.1; 530/387.2; 530/387.9; 530/388.1; 530/388.15; 530/388.2; 530/388.25; 530/388.7; 424/9.1; 424/130.1; 424/131.1; 424/133.1; 424/134.1; 514/1; 514/2; 435/4; 435/7.1; 435/41; 435/69.1
(58) Field of Search ............ 530/350, 380, 530/385, 386, 387.1, 387.2, 387.9, 388.1, 388.15, 388.2, 388.25, 388.7, 300, 324; 514/1, 2; 424/9.1, 130.1, 131.1, 133.1, 134.1; 435/4, 7.1, 41, 69.1

(56) References Cited

FOREIGN PATENT DOCUMENTS

WO   WO 98/06838   2/1998

OTHER PUBLICATIONS

Amino acid database, Accession # P48960, 1996.*

Amino acid database, Accession # I37225, 1996.*

Rojanasakul, Y. Antisense oligonucleotide therapeutics: drug delivery and targeting. Advanced Drug Delivery Reviews 18:115–131, 1996.*

Hamann, J. et al., *J. of Immunology*, 155(4):1942–1950 (1995).

Hamann, J. et al., *Genomics*, 32(1):144–147 (1996).

Hamann, J. et al., *J. of Experimental Medicine*, 184(3):1185–1189 (1996).

Hamann, J. et al., *J. of Cellular Biochemistry Supplement* 0(21 A):72 (1995).

Gray, J. et al., *J. of Immunology* 157(12):5438–5447 (1996).

Eichler, W., et al., *Tissue Antigens* 50(5):429–438 (1997).

Aust. G., et al., *Cancer Research* 57(9): 1798–1806 (1997).

* cited by examiner

*Primary Examiner*—Sheela Huff
*Assistant Examiner*—Alana M. Harris
(74) *Attorney, Agent, or Firm*—Townsend and Townsend and Crew LLP

(57) ABSTRACT

Isolated proteins comprising the T-cell surface antigen CD97 α are provided. Compositions and methods for making and detecting CD97 α are also provided. Further, the invention provides diagnostic and therapeutic methods and compositions for medical conditions involving CD97.

9 Claims, 5 Drawing Sheets

|       |      | FIG. 1A |
|-------|------|---------|
|       |      | FIG. 1B |
| FIG. 1|      | FIG. 1C |

```
 -48                                                    CTGTCCCACTCACTCTTTCCCCTGCCGCTCCTGCCGGCAGCTCCAACC
   1 ATGGGAGGCCGCGTCTTTCTGGCATTCTGTGTCTGGCTGACTCTGCCCGGGGCTGAAACCCAGGACTCTGAAACTCAGGACTGTGCCCGGTGTGC    30
     M  G  G  R  V  F  L  A  F  C  V  W  L  T  L  P  G  A  E  T  Q  D |S  R  G  C  A  R  W  C |
  91 CCTCAGAACTCCTGCGTCGTGTCAATGCCACCGCCTGCGCTGCAGAATCCAGGGTTCAGCTCTCTTTTCTGAGATCATCACCCCGACGGAG        60
    |P  Q  N  S  S  C  V  N| A  T  A  C  R  C |N  P  G  F  S  F  S  E  I  I  T  P  T  E|
 181 ACTTGTGACGACATCAACGAGTGTGCCACACCGTCGAAAGTGTCATGCGGGAAAATTCTGGACTGCTGGAACACAGAGGGAGCTACGAC         90
    |T  C  D |D  I  N  E  C  A  T  P  S  K  V  S  C  G  K  F  S  D  C  W  N  T  E  G  S  Y  D|
 271 TGCGTGTGCAGCCCGGGATATGAGCCTGTTTCTGGGACAAAGACATTCAAGAATGAGAGCGAGAACACCTGTCAAGATGTGACGAATGT        120
    |C  V  C  S  P  G  Y  E  P  V  S  G  T  K  T  F  K  N  E  S  E  N  T  C  Q |D  V  D  E  C|
 361 CAGCAGAACCCAAGGCTCTGTAAAGTCTGCACAGATGTGAATGAATCCCGGACACTACCTGCCAGTGCCTATACCTGCCAGCTCCAACAAC      150
    |Q  Q  N  P  R  L  C  K  S  Y  G  T  C  V  N  T  L  G  S  Y  T  C  Q  C  L  P  G  F  F  F|
 451 ATACCTGAGGATCCGAAGGTCTGCGAAGTTGCCACACAGATGTGAATGAATGCCGTCCCACAGTCGCCACTCCCAACAAC                180
    |I  P  E  D  P  K  V  C  T |D  V  N  E  C |S  G  Q  N  P  C  H  S  S  T  H  C  L  N  N|
 541 GTGGGCAGCTATCAGTGTCGTGTGCAGCCTGGCCAAATGCCCAAACAATACCGTTCGTGAAGATGTG                              210
    |V  G  S  Y  Q  C  R  C  R  P  G  M  Q  P  I  P  G  S  P  N  G  P  N  N  T  V  C |E |D  V |
 631 GACGAGTGCAGCAGTGGGCAGCATCAGTGTGACAGCAGCACTGTGTGCTTCAACACCGTGGGTTCATACAGCTGCCGCTGCCGCCCAGGC      240
    |D  E  C  S  S  G  Q  H  Q  C  D  S  S  T  V  C  F  N  T  V  G  S  Y  S  C  R  C  R  P  G|
 721 TGGAAGCCCAGACACGGAATCCCGAATAACCAAAAGGACACTGTCTGTGAAGATATGACTTTCTCCACCTGGACCCCCCCTGGAGTC         270
     W  K  P  R  H  G  I  P  N  N  Q  K  D  T  V  C |E  D  M  T  F  S  T  W  T  P  P  P  G  V
 811 CACGCCAGAGCTTTCCCGATTCTTCGACAAAGTCCAAGACTCCAAGAGACTCCAAGTCGAGTCACCATCCAGAAT                     300
     H  S  Q  T  L  S  R  F  F  D  K  V  Q  D  L  G  R  D  S  K  T  S  S  A  E  V  T  I  Q  N
```

| FIG. 1A |
| FIG. 1B |
| FIG. 1C |

```
901  GTCATCAAATTGGTGATGAACTGATGGAAGCTCCTGGAGACGTAGAGGCCCTGGCGCCACCTGTCCGGCACCTCATAGCCACCCAGCTG   330
      V  I  K  L  V  D  E  L  M  E  A  P  G  D  V  E  A  L  A  P  P  V  R  H  L  I  A  T  Q  L

991  CTCTCAAACCTTGAAGATATCATGAGGATCCTGGCCAAGAGCCTGCCTAAAGGCCCCTTCACTTACATTTCCCCTTCGAACACAGAGCTG   360
      L  S  N  L  E  D  I  M  R  I  L  A  K  S  L  P  K  G  P  F  T  Y  I  S  P  S  N  T  E  L

1081 ACCCTGATGATCCAGGAGTGTCACTATGGGTCAGAGCAGCGCCATGAAGCTGAATTGGGCTGTGGCAGCTGGA   390
      T  L  M  I  Q  E ⟨K⟩ V  T  M  G  Q  S  S  A  R  M  K  L  N  W  A  V  A  A  G

1171 GCCGAGGATCCAGGCCCCGCCGTGGCGGGGATCCTCTCCATCCAGAACATGACGACATTGCTGGCCAATCTGAACCTGCATTCC   420
      A  E  D  P  G  P  A  V  A  G  I  L  S  I  Q ⟨N⟩ M  T  T  L  L  A  A  S  L  N  L  H  S

1261 AAGAAGCAAGCCAACACCAAGGAACTGAAGGAGATATATGAAGAGCATCCGTGTGTCCAACTCAGACGCCTCTCTGCCGTCAACTCTTTCTG   450
      K  K  Q  A  E  L  E  E  I  Y  E  S  S  I  R  G  V  Q  L  R  R  L  S  A  V  N  S  I  F  L

1351 AGCCACAACAACAAGAACTCAACTCCCCCCATCCTTTTCGCCTTCTCCCACCTTGAGTCCTCCGATGGGGAGGCGGAAGAGACCCT   480
      S  H ⟨N⟩ T  K  E  L  N  S  P  I  L  F  A  F  S  H  L  E  S  S  D  G  E  A  G  R  D  P

1441 CCTGCCAAGGACGTGATGCCTGGCCCCAGGCAGGAGCTGCTGTGCGCCTTTTGGAAGAGTGACAGGGGAGGCCACTGGGCCACC   510
      P  A  K  D  V  M  P  G  P  R  Q  E  L  L  C  A  F  W  K  S  D  R  G  G  H  W  A  T

1531 GAGGGCTGCCAAGTGCTGGGTAGCAAGGGCTCGACCTGCCAGTGTTCACTCCTGTGCATCCTTGACTTTCCTT   540
      E  G  C  Q  V  L  G  S  K ⟨N⟩ G  S  T  C  Q  C  S  H  L  S  S  F  A  I  L  M  A  H  Y

1621 GACGTGGAGGACTGGAAGCTGACCCTGATCACCAGGGTTGGGTTGGCTCTGTCCCTCTGCTTCTGCCTCCTGCTCTGCATCCTCACTTTCCTG   570
      D  V  E  D  W  K  L  T  L  I  T  R  V  G  L  A  L  S  L  F  C  L  L  L  C  I  L  T  F  L

1711 CTGTGTGGCGGCAGCCGCACCATACACCTGCACCTGTGCATCTGCCTCTTCGTGGGCTCCACCATCTTCCTGGCCGGC   600
      L  C  G  S  R  T  T  I  H  L  H  L  C  I  C  L  F  V  G  S  T  I  F  L  A  G

1801 ATCGAGAACGAAGGCGGCCAGGTGGGGCTGCGCTGCCGCCTCGTGGCTGGCCTGCTGCACTACTGTTTCCTGGCCGCCTTCTGCTGGATG   630
      I  E  N  E  G  G  Q  V  G  L  R  C  R  L  V  A  G  L  L  H  Y  C  F  L  A  A  F  C  W  M
```

```
1891 AGCCTCGAAGGCCTGGAGCTCTACTTTCTGTGTGGTGCGCGTGTTCCAAGGCCAAGGCCTGAGTACGGCCTGCTCTGCCTGATCGGCTAT
      S  L  E  G  L  E  L  Y  F  L  V  V  R  V  F  Q  G  Q  G  L  S  T  R  W  L  C  L  I  G  Y    660
1981 GGCGTGCCCCTGCTCATCGTGGGCGTCTCGGCTGCCATCTACAGCAAGGGCTACGGCCGCCCCAGATACTGCTGTGTTGACTTTGAGCAG
      G  V  P  L  L  I  V  G  V  S  A  A  I  Y  S  K  G  Y  G  R  P  R  Y  C  W  L  D  F  E  Q    690
2071 GGCTTCCTCTGGAGCTTCTTGGGACCTGTGACCTTCATCATTTTGTGCAATGCTGTCATTTTCGTGACTACCGTCTGGAAGCTCACTCAG
      G  F  L  W  S  F  L  G  P  V  T  F  I  I  L  C  N  A  V  I  F  V  T  T  V  W  K  L  T  Q    720
2161 AAGTTTTCTGAAATCAATCCAGACATGAAGAAGAAATTAAAGAAGGCGCGTCTGACCATCGCGCAGCTCTTCCTGTTGGC
      K  F  S  E  I  N  P  D  M  K  K  K  L  K  K  A  R  A  L  T  I  A  Q  L  F  L  L  G          750
2251 TGCACACTGGGTCTTTGGCCTGTTCATCTTCGACGATCGAAGCTTGGTGCTGACCTATGTGTTACCATCTGCTTGAACTGCCTGCAGGCGCC
      C  T  W  V  F  G  L  F  I  F  D  D  R  S  L  V  T  Y  V  F  T  I  L  N  C  L  Q  G  A       780
2341 TTCCTCTACCTGCTACTGCACTGCCTGCTCAACAAGAAGGTTCGGGAAGAATACCGGAAGTGGGCCATCGAGAGTTCCGGACATGAAGGCGCATGTT
      F  L  Y  L  L  H  C  L  L  N  K  K  V  R  E  E  Y  R  K  W  A  C  L  V  A  G  G  S  K  Y    810
2431 TCAGAATTCACTTCCACTTCAGGTACCGGTCACAATCAGACCCGGGCCCTGCGTGCCAGCGAAAGCGGCATC
      S  E  F  T  S  T  T  S  G  T  G  H  N  Q  T  R  A  L  R  A  S  E  S  G  I
2521 CTGGACGGGCCCAGCAGCTGCTGTGGCCACAGCAGCTTTGTACGACGAAGACCATCATCCCTCGTCCACCACTCTACTCCCTCCACC
2611 CTCCCTCCCCTGATCCCAGTCCGTGCAGCAGGAGGAGTGGCAGTAGTCTCAGGACACCCAGTGGGTGGAGTCGGAG
2701 CCACTGGTCCTGCTCGTGGCTGCGTCTGTCCCACCTGTGACCCAGGGGCTGGCCCAGGAGCTGCCAATGCAGCATGTT
2791 GCCCTAGGCACCTGGGCTGGGGCTGGCCAGTACTCGGGACAGATCGGGACTTTGTCCATGCTGCTTGCTCAGAACTGA
2881 AGAGACTAGGCGCTAGGGCCTCAGCTTCCCTTGGCGCGCCTGCCTGGCTGCGGGCAGGAGTAAGACTAAGCTAAGGCCCATGCTGAGGCCCTTGGGCCACTGCCTGAG
2971 GCTCACGTACAGAGGCTACGTGTTGACACTTAAAATTAAAACACATGCATACAG
3061 GTTAAATTTTCAGTGTTGACACTTAAAATTAAAACACATGCATACAG
```

FIG. 1C

```
       EGF#1  DSRGCARW....CPQNSSCVNATA...CRCNPGFSSFSEIITPTE...TCD
       EGF#2  DINECATPSKVSCGKFSDCWNTEGSYDCVCSPGYEPVSGTKTFKNESENTCQ
CD97   EGF#3  DVDECQQNPRL.CKSYGTCVNTLGSYTCQCLPGFKFIP.......EDPKVCT
       EGF#4  DVNECTSGQNP.CHSSTHCLNNVGSYQCRCRPGWQPIPGSPNGPNNT..VCE
       EGF#5  DVDECSSGQHQ.CDSSTVCFNTVGSYSCRCRPGWKPRHGIPNNQKDT..VCE

FIBRILLIN     DIDEC------.C--G-.C-NT-GSY-C-C---GF----------...C.
EMR1          DIDEC------.C------.C-N--G-Y-C-C---GF-----------  C
(REPEAT 2-6)  VN  *              *              *              *

D/N β
HYDROXYLATION           CXDXXXXYXCXC
CONSENSUS               (N)    (E)
```

FIG. 3.

SEQUENCE LISTING

<160> NUMBER OF SEQ ID NOS: 21

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence:EGF-1
      EGF-like repeat conserved motif

<400> SEQUENCE: 1

Asp Ser Arg Gly Cys Ala Arg Trp Cys Pro Gln Asn Ser Ser Cys Val
 1               5                  10                  15

Asn Ala Thr Ala Cys Arg Cys Asn Pro Gly Phe Ser Ser Phe Ser Glu
            20                  25                  30

Ile Ile Thr Thr Pro Thr Glu Thr Cys Asp
        35                  40

<210> SEQ ID NO 2
<211> LENGTH: 52
<212> TYPE: PRT
<213> ORGANISM: Artificial Sequence
<220> FEATURE:
<223> OTHER INFORMATION: Description of Artificial Sequence:EGF-2
      EGF-like repeat conserved motif

<400> SEQUENCE: 2

Asp Ile Asn Glu Cys Ala Thr Pro Ser Lys Val Ser Cys Gly Lys Phe
 1               5                  10                  15

Ser Asp Cys Trp Asn Thr Glu Gly Ser Tyr Asp Cys Val Cys Ser Pro
            20                  25                  30

Gly Tyr Glu Pro Val Ser Gly Thr Lys Thr Phe Lys Asn Glu Ser Glu
            35                  40                  45

Asn Thr Cys Gln
        50

<210> SEQ ID NO 3
<211> LENGTH: 44
<212> TYPE: PRT
<213> ORGANISM: Artificial Sequence

```
<220> FEATURE:
<223> OTHER INFORMATION: Description of Artificial Sequence:EGF-3
      EGF-like repeat conserved motif

<400> SEQUENCE: 3

Asp Val Asp Glu Cys Gln Gln Asn Pro Arg Leu Cys Lys Ser Tyr Gly
 1               5                  10                  15

Thr Cys Val Asn Thr Leu Gly Ser Tyr Thr Cys Gln Cys Leu Pro Gly
            20                  25                  30

Phe Lys Phe Ile Pro Glu Asp Pro Lys Val Cys Thr
        35                  40

<210> SEQ ID NO 4
<211> LENGTH: 49
<212> TYPE: PRT
<213> ORGANISM: Artificial Sequence
<220> FEATURE:
<223> OTHER INFORMATION: Description of Artificial Sequence:EGF-4
      EGF-like repeat conserved motif

<400> SEQUENCE: 4

Asp Val Asn Glu Cys Thr Ser Gly Gln Asn Pro Cys His Ser Ser Thr
 1               5                  10                  15

His Cys Leu Asn Asn Val Gly Ser Tyr Gln Cys Arg Cys Arg Pro Gly
            20                  25                  30

Trp Gln Pro Ile Pro Gly Ser Pro Asn Gly Pro Asn Asn Thr Val Cys
        35                  40                  45

Glu

<210> SEQ ID NO 5
<211> LENGTH: 49
<212> TYPE: PRT
<213> ORGANISM: Artificial Sequence
<220> FEATURE:
<223> OTHER INFORMATION: Description of Artificial Sequence:EGF-5
      EGF-like repeat conserved motif

<400> SEQUENCE: 5

Asp Val Asp Glu Cys Ser Ser Gly Gln His Gln Cys Asp Ser Ser Thr
 1               5                  10                  15

Val Cys Phe Asn Thr Val Gly Ser Tyr Ser Cys Arg Cys Arg Pro Gly
            20                  25                  30

Trp Lys Pro Arg His Gly Ile Pro Asn Asn Gln Lys Asp Thr Val Cys
        35                  40                  45

Glu

<210> SEQ ID NO 6
<211> LENGTH: 835
<212> TYPE: PRT
<213> ORGANISM: Homo sapiens
<220> FEATURE:
<223> OTHER INFORMATION: CD97amino acid sequence encoded by full-length
      clone pAT276

<400> SEQUENCE: 6

Met Gly Gly Arg Val Phe Leu Ala Phe Cys Val Trp Leu Thr Leu Pro
 1               5                  10                  15

Gly Ala Glu Thr Gln Asp Ser Arg Gly Cys Ala Arg Trp Cys Pro Gln
            20                  25                  30

Asn Ser Ser Cys Val Asn Ala Thr Ala Cys Arg Cys Asn Pro Gly Phe
        35                  40                  45
```

```
Ser Ser Phe Ser Glu Ile Ile Thr Thr Pro Thr Glu Thr Cys Asp Asp
    50                  55                  60

Ile Asn Glu Cys Ala Thr Pro Ser Lys Val Ser Cys Gly Lys Phe Ser
65                  70                  75                  80

Asp Cys Trp Asn Thr Glu Gly Ser Tyr Asp Cys Val Cys Ser Pro Gly
                85                  90                  95

Tyr Glu Pro Val Ser Gly Thr Lys Thr Phe Lys Asn Glu Ser Glu Asn
            100                 105                 110

Thr Cys Gln Asp Val Asp Glu Cys Gln Gln Asn Pro Arg Leu Cys Lys
        115                 120                 125

Ser Tyr Gly Thr Cys Val Asn Thr Leu Gly Ser Tyr Thr Cys Gln Cys
    130                 135                 140

Leu Pro Gly Phe Lys Phe Ile Pro Glu Asp Pro Lys Val Cys Thr Asp
145                 150                 155                 160

Val Asn Glu Cys Thr Ser Gly Gln Asn Pro Cys His Ser Ser Thr His
                165                 170                 175

Cys Leu Asn Asn Val Gly Ser Tyr Gln Cys Arg Cys Arg Pro Gly Trp
            180                 185                 190

Gln Pro Ile Pro Gly Ser Pro Asn Gly Pro Asn Asn Thr Val Cys Glu
        195                 200                 205

Asp Val Asp Glu Cys Ser Ser Gly Gln His Gln Cys Asp Ser Ser Thr
    210                 215                 220

Val Cys Phe Asn Thr Val Gly Ser Tyr Ser Cys Arg Cys Arg Pro Gly
225                 230                 235                 240

Trp Lys Pro Arg His Gly Ile Pro Asn Asn Gln Lys Asp Thr Val Cys
                245                 250                 255

Glu Asp Met Thr Phe Ser Thr Trp Thr Pro Pro Gly Val His Ser
            260                 265                 270

Gln Thr Leu Ser Arg Phe Phe Asp Lys Val Gln Asp Leu Gly Arg Asp
        275                 280                 285

Ser Lys Thr Ser Ser Ala Glu Val Thr Ile Gln Asn Val Ile Lys Leu
    290                 295                 300

Val Asp Glu Leu Met Glu Ala Pro Gly Asp Val Glu Ala Leu Ala Pro
305                 310                 315                 320

Pro Val Arg His Leu Ile Ala Thr Gln Leu Leu Ser Asn Leu Glu Asp
                325                 330                 335

Ile Met Arg Ile Leu Ala Lys Ser Leu Pro Lys Gly Pro Phe Thr Tyr
            340                 345                 350

Ile Ser Pro Ser Asn Thr Glu Leu Thr Leu Met Ile Gln Glu Arg Gly
        355                 360                 365

Asp Lys Asn Val Thr Met Gly Gln Ser Ser Ala Arg Met Lys Leu Asn
    370                 375                 380

Trp Ala Val Ala Ala Gly Ala Glu Asp Pro Gly Pro Ala Val Ala Gly
385                 390                 395                 400

Ile Leu Ser Ile Gln Asn Met Thr Thr Leu Leu Ala Asn Ala Ser Leu
                405                 410                 415

Asn Leu His Ser Lys Lys Gln Ala Glu Leu Glu Glu Ile Tyr Glu Ser
            420                 425                 430

Ser Ile Arg Gly Val Gln Leu Arg Arg Leu Ser Ala Val Asn Ser Ile
        435                 440                 445

Phe Leu Ser His Asn Asn Thr Lys Glu Leu Asn Ser Pro Ile Leu Phe
    450                 455                 460

Ala Phe Ser His Leu Glu Ser Ser Asp Gly Glu Ala Gly Arg Asp Pro
```

```
                    465                 470                 475                 480

Pro Ala Lys Asp Val Met Pro Gly Pro Arg Gln Glu Leu Leu Cys Ala
                485                 490                 495

Phe Trp Lys Ser Asp Ser Asp Arg Gly Gly His Trp Ala Thr Glu Gly
            500                 505                 510

Cys Gln Val Leu Gly Ser Lys Asn Gly Ser Thr Thr Cys Gln Cys Ser
        515                 520                 525

His Leu Ser Ser Phe Ala Ile Leu Met Ala His Tyr Asp Val Glu Asp
    530                 535                 540

Trp Lys Leu Thr Leu Ile Thr Arg Val Gly Leu Ala Leu Ser Leu Phe
545                 550                 555                 560

Cys Leu Leu Leu Cys Ile Leu Thr Phe Leu Leu Val Arg Pro Ile Gln
                565                 570                 575

Gly Ser Arg Thr Thr Ile His Leu His Leu Cys Ile Cys Leu Phe Val
                580                 585                 590

Gly Ser Thr Ile Phe Leu Ala Gly Ile Glu Asn Glu Gly Gly Gln Val
            595                 600                 605

Gly Leu Arg Cys Arg Leu Val Ala Gly Leu Leu His Tyr Cys Phe Leu
        610                 615                 620

Ala Ala Phe Cys Trp Met Ser Leu Glu Gly Leu Glu Leu Tyr Phe Leu
625                 630                 635                 640

Val Val Arg Val Phe Gln Gly Gln Gly Leu Ser Thr Arg Trp Leu Cys
                645                 650                 655

Leu Ile Gly Tyr Gly Val Pro Leu Leu Ile Val Gly Val Ser Ala Ala
                660                 665                 670

Ile Tyr Ser Lys Gly Tyr Gly Arg Pro Arg Tyr Cys Trp Leu Asp Phe
            675                 680                 685

Glu Gln Gly Phe Leu Trp Ser Phe Leu Gly Pro Val Thr Phe Ile Ile
        690                 695                 700

Leu Cys Asn Ala Val Ile Phe Val Thr Thr Val Trp Lys Leu Thr Gln
705                 710                 715                 720

Lys Phe Ser Glu Ile Asn Pro Asp Met Lys Lys Leu Lys Lys Ala Arg
                725                 730                 735

Ala Leu Thr Ile Thr Ala Ile Ala Gln Leu Phe Leu Leu Gly Cys Thr
                740                 745                 750

Trp Val Phe Gly Leu Phe Ile Phe Asp Asp Arg Ser Leu Val Leu Thr
            755                 760                 765

Tyr Val Phe Thr Ile Leu Asn Cys Leu Gln Gly Ala Phe Leu Tyr Leu
        770                 775                 780

Leu His Cys Leu Leu Asn Lys Lys Val Arg Glu Glu Tyr Arg Lys Trp
785                 790                 795                 800

Ala Cys Leu Val Ala Gly Gly Ser Lys Tyr Ser Glu Phe Thr Ser Thr
                805                 810                 815

Thr Ser Gly Thr Gly His Asn Gln Thr Arg Ala Leu Arg Ala Ser Glu
            820                 825                 830

Ser Gly Ile
        835

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence:RGD motif
      binding site for several classes of integrins
```

<400> SEQUENCE: 7

Arg Gly Asp
 1

<210> SEQ ID NO 8
<211> LENGTH: 3156
<212> TYPE: DNA
<213> ORGANISM: Homo sapiens
<220> FEATURE:
<223> OTHER INFORMATION: full length pAT276 encoding CD97
<220> FEATURE:
<221> NAME/KEY: CDS
<222> LOCATION: (49)..(2556)
<223> OTHER INFORMATION: CD97

<400> SEQUENCE: 8

```
ctgtcccact cactctttcc cctgccgctc ctgccggcag ctccaaccat gggaggccgc     60
gtctttctcg cattctgtgt ctggctgact ctgccgggag ctgaaaccca ggactccagg    120
ggctgtgccc ggtggtgccc tcagaactcc tcgtgtgtca atgccaccgc ctgtcgctgc    180
aatccagggt tcagctcttt ttctgagatc atcaccaccc cgacggagac ttgtgacgac    240
atcaacgagt gtgcaacacc gtcgaaagtg tcatgcggaa aattctcgga ctgctggaac    300
acagagggga gctacgactg cgtgtgcagc ccgggatatg agcctgtttc tgggacaaaa    360
acattcaaga atgagagcga gaacacctgt caagatgtgg acgaatgtca gcagaaccca    420
aggctctgta aaagctacgg cacctgcgtc aacacccttg cagctatac ctgccagtgc    480
ctgcctggct tcaagttcat acctgaggat ccgaaggtct gcacagatgt gaatgaatgc    540
acctccggac aaaatccgtg ccacagctcc acccactgcc tcaacaacgt gggcagctat    600
cagtgtcgct gccgaccggg ctggcaaccg attccggggt cccccaatgg cccaaacaat    660
accgtctgtg aagatgtgga cgagtgcagc tccgggcagc atcagtgtga cagctccacc    720
gtctgcttca cacccgtggg ttcatacagc tgccgctgcc gcccaggctg gaagcccaga    780
cacggaatcc gaataaccaa aaggacactg tctgtgaag atatgacttt ctccaccctgg    840
acccccgccc ctggagtcca gccagacg ctttcccgat tcttcgacaa agtccaggac    900
ctgggcagag actccaagac aagctcagcc gaggtcacca tccagaatgt catcaaattg    960
gtggatgaac tgatggaagc tcctggagac gtagaggccc tggcgccacc tgtccggcac   1020
tcatagcca cccagctgct ctcaaacctt gaagatatca tgaggatcct ggccaagagc   1080
ctgcctaaag gccccttcac ctacatttcc ccttcgaaca cagagctgac cctgatgatc   1140
caggagcggg gggacaagaa cgtcactatg ggtcagagca gcgcacgcat gaagctgaat   1200
tgggctgtgg cagctggagc cgaggatcca ggccccgccg tggcgggcat cctctccatc   1260
cagaacatga cgacattgct ggccaatgcc tccttgaacc tgcattccaa gaagcaagcc   1320
gaactggagg agatatatga agcagcatcc gtggtgtcc aactcagacg cctctctgcc   1380
gtcaactcca tctttctgag ccacaacaac accaaggaac tcaactcccc catccttttc   1440
gccttctccc accttgagtc ctccgatggg gaggcgggaa gagaccctcc tgccaaggac   1500
gtgatgcctg ggccacggca ggagctgctc tgtgccttct ggaagagtga cagcgacagg   1560
ggagggcact gggccaccga gggctgccag gtgctgggca caagaacgg cagcaccacc   1620
tgccaatgca gccacctgag cagctttgcg atccttatgg ctcattatga cgtggaggac   1680
tggaagctga cctgatcac cagggtggga ctggcgctgt cactcttctg cctgctgctg   1740
tgcatcctca ctttcctgct ggtgcggccc atccagggct cgcgcaccac catacacctg   1800
```

```
cacctctgca tctgcctctt cgtgggctcc accatcttcc tggccggcat cgagaacgaa    1860
ggcggccagg tggggctgcg ctgccgcctg gtggccgggc tgctgcacta ctgtttcctg    1920
gccgccttct gctggatgag cctcgaaggc ctggagctct actttcttgt ggtgcgcgtg    1980
ttccaaggcc agggcctgag tacgcgctgg ctctgcctga tcggctatgg cgtgcccctg    2040
ctcatcgtgg gcgtctcggc tgccatctac agcaagggc acggccgccc cagatactgc    2100
tggttggact ttgagcaggg cttcctctgg agcttcttgg gacctgtgac cttcatcatt    2160
ttgtgcaatg ctgtcatttt cgtgactacc gtctggaagc tcactcagaa gttttctgaa    2220
atcaatccag acatgaagaa attaaagaag gcgagggcgc tgaccatcac ggccatcgcg    2280
cagctcttcc tgttgggctg cacctgggtc tttggcctgt tcatcttcga cgatcggagc    2340
ttggtgctga cctatgtgtt taccatcctc aactgcctgc agggcgcctt cctctacctg    2400
ctgcactgcc tgctcaacaa gaaggttcgg gaagaatacc ggaagtgggc ctgcctagtt    2460
gctgggggga gcaagtactc agaattcacc tccaccacgt ctggcactgg ccacaatcag    2520
acccgggccc tcagggcatc agagtccggc atatgaaggc gcatggttct ggacggccca    2580
gcagctcctg tggccacagc agctttgtac acgaagacca tccatcctcc cttcgtccac    2640
cactctactc cctccaccct ccctccctga tcccgtgtgc caccaggagg gagtggcagc    2700
tatagtctgg caccaaagtc caggacaccc agtggggtgg agtcggagcc actggtcctg    2760
ctgctggctg cctctctgct ccaccttgtg acccagggtg gggacagggg ctggcccagg    2820
gctgcaatgc agcatgttgc cctggcacct gtggccagta ctcgggacag actaagggcg    2880
cttgtcccat cctggacttt tcctctcatg tctttgctgc agaactgaag agactaggcg    2940
ctggggctca gcttccctct taagctaaga ctgatgtcag aggccccatg gcgaggcccc    3000
ttggggccac tgcctgaggc tcacggtaca gaggcctgcc ctgcctggcc gggcaggagg    3060
ttctcactgt tgtgaaggtt gtagacgttg tgtaatgtgt ttttatctgt taaaattttt    3120
cagtgttgac acttaaaatt aaacacatgc atacag                              3156
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:5' PCR
      primer 276-38

<400> SEQUENCE: 9

```
ggccgcgtct ttctcgca                                                    18
```

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:5' PCR
      primer 276-20

<400> SEQUENCE: 10

```
agatgtggac gaatgtc                                                     17
```

<210> SEQ ID NO 11
<211> LENGTH: 17
<212> TYPE: DNA
<213> ORGANISM: Artificial Sequence
<220> FEATURE:

```
<223> OTHER INFORMATION: Description of Artificial Sequence:5' PCR
      primer 276-6A

<400> SEQUENCE: 11
aagacaagct cagccga                                                    17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:3' PCR
      primer 276-3

<400> SEQUENCE: 12
tgggttcata cagctgc                                                    17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:3' PCR
      primer 276-6B

<400> SEQUENCE: 13
tcggctgagc ttgtctt                                                    17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:3' PCR
      primer 276-15B

<400> SEQUENCE: 14
gcagctgtat gaaccca                                                    17

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence:anti-EGF3
      peptide used for antibody production

<400> SEQUENCE: 15

Cys Leu Pro Gly Phe Lys Phe Ile Pro Glu Asp Pro Lys Val Cys
 1               5                  10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence:anti-COOH
      peptide used for antibody production

<400> SEQUENCE: 16

Glu Phe Thr Ser Thr Thr Ser Gly Thr Gly His Asn Gln Thr Arg Ala
 1               5                  10                  15

<210> SEQ ID NO 17
<211> LENGTH: 32
<212> TYPE: DNA
<213> ORGANISM: Artificial Sequence
```

```
<220> FEATURE:
<223> OTHER INFORMATION: Description of Artificial Sequence:
      oligonucleotide amplification primer

<400> SEQUENCE: 17
atgggaggcc gcgtctttct cgcattctgt gt                                    32

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:
      oligonucleotide amplification primer

<400> SEQUENCE: 18
gggccctcag ggcatcagag tccggcata                                        29

<210> SEQ ID NO 19
<211> LENGTH: 41
<212> TYPE: PRT
<213> ORGANISM: Artificial Sequence
<220> FEATURE:
<223> OTHER INFORMATION: Description of Artificial Sequence:EGF-like
      repeat conserved motif in fibrillin
<220> FEATURE:
<221> NAME/KEY: MOD_RES
<222> LOCATION: (1)..(41)
<223> OTHER INFORMATION: Xaa = any amino acid

<400> SEQUENCE: 19

Asp Ile Asp Glu Cys Xaa Xaa Xaa Xaa Xaa Cys Xaa Xaa Gly Xaa
 1               5                  10                  15

Cys Xaa Asn Thr Xaa Gly Ser Tyr Xaa Cys Xaa Cys Xaa Xaa Gly Phe
             20                  25                  30

Xaa Xaa Xaa Xaa Xaa Xaa Xaa Xaa Cys
         35                  40

<210> SEQ ID NO 20
<211> LENGTH: 48
<212> TYPE: PRT
<213> ORGANISM: Artificial Sequence
<220> FEATURE:
<223> OTHER INFORMATION: Description of Artificial Sequence:EGF-like
      repeat conserved motif in EMR1
<220> FEATURE:
<221> NAME/KEY: MOD_RES
<222> LOCATION: (1)..(48)
<223> OTHER INFORMATION: Xaa = any amino acid

<400> SEQUENCE: 20

Asp Ile Asp Glu Cys Xaa Xaa Xaa Xaa Xaa Xaa Cys Xaa Xaa Xaa Xaa
 1               5                  10                  15

Xaa Cys Xaa Asn Xaa Xaa Gly Xaa Tyr Xaa Cys Xaa Cys Xaa Xaa Gly
             20                  25                  30

Phe Xaa Xaa Xaa Xaa Xaa Xaa Xaa Xaa Xaa Xaa Xaa Xaa Xaa Xaa Cys
         35                  40                  45

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence:Asp/Asn
      beta-hydroxylation consensus motif
<220> FEATURE:
<221> NAME/KEY: MOD_RES
```

-continued

```
<222> LOCATION: (1)..(12)
<223> OTHER INFORMATION: Xaa = any amino acid

<400> SEQUENCE: 21

Cys Xaa Xaa Xaa Xaa Xaa Xaa Xaa Xaa Cys Xaa Cys
 1               5                  10
```

METHODS AND COMPOSITIONS FOR INHIBITING INFLAMMATION AND ANGIOGENESIS COMPRISING A MAMMALIAN CD97 α SUBUNIT

CROSS-REFERENCE TO RELATED APPLICATIONS

This application claims priority to provisional application No. 60/027,871, filed Oct. 25, 1996 and is herein incorporated by reference.

FEDERALLY SPONSORED RESEARCH AND DEVELOPMENT

This invention was funded through the intramural program of the Division of Clinical Science of the National Cancer Institute.

BACKGROUND OF THE INVENTION

Ligation of the T-cell receptor initiates a cascade of intracellular signaling events resulting in the proliferation and differentiation of the activated cell. Many of the phenotypic changes which define T-cell activation result from new gene transcription (Ullman, et al., *Annu. Rev. Immunol.* 8:421–452 (1990)). Activation-induced changes in cell surface proteins resulting from a primary stimulus play a particularly important role in regulating downstream proliferative and differentiative responses. Events mediated at the cell surface include binding of soluble factors and interactions with other cells and extracellular matrix. In vivo, activated T cells play an instrumental role in the propagation of immunologically mediated inflammation (Brezinschek, et al., *J. Immunol.*, 154:3062–77 (1995)).

The development and progression of inflammation is dependent upon the infiltration of leukocytes into the affected tissues. The accumulation of leukocytes into tissues involves receptor-mediated interactions with the endothelial cell lining of postcapillary venules, extravasation, and migration toward and localization within the inflammatory site (Shimizu, et al., *FASEB J.* 5:2292–2299 (1992)). A large body of work has shown that the combinatorial use of multiple adhesion and chemoattractant receptors appears to regulate selection of subclasses of leukocytes emigrating at inflammatory sites as well as the distinctive recirculation behavior of lymphocyte subsets (Springer, *Cell* 76:301–314 (1994)). Little is known about the range of receptor-ligand interactions in leukocytes that regulate their localization within the tissue microenvironment following extravasation.

Once at the site of inflammation, immune cells undergo additional phenotypic changes that contribute to eliminating the foreign antigen and to amplifying the inflammatory response. Various soluble mediators of inflammation such as prostaglandins, leukotrienes, complement fragments, platelet-activating factors, chemokines, and formyl peptides, among others (Murphy, *Annu. Rev. Immunol.* 12:593–633 (1994)) bind to specific receptors that are part of a very large and diverse class of receptors that span the membrane seven times (7TM receptors). 7TM receptors, also called G protein coupled receptors, transduce signals following ligand binding via their association with heterotrimeric G proteins (Martens, PROGRESS IN BRAIN RESEARCH, Joose, et al., (eds.), pp. 201–214 (1992)). Receptor coupled G protein activation in turn regulates a variety of enzymes (such as adenyl cyclase, phospholipase Cb, phosphoinositide 3-kinase), ion channels and transporters (Neer, *Cell* 80:249–257 (1995)).

The family of 7TM receptors is probably the largest receptor family known, a with hundreds of receptors cloned to date. The receptors bind a wide structural array of ligands including various types of hormones, neurotransmitters, lipids, peptides, and odorants (Spiegel, G PROTEINS, Spiegel., et al., (eds.), R. G. Landes Co., Austin. pp. 6–17 (1994)). The defining feature and the areas of greatest homology among the 7TM receptors are in the seven transmembrane regions (Probst, et al., *DNA and Cell Biol.* 11:1–20 (1992)). Some residues are found in virtually all 7TM receptors and may mediate evolutionarily-conserved tertiary structural requirements for functional activity. Other residues are conserved among subfamilies that bind similar ligands and have been shown to contribute to ligand binding and/or specificity (Savarese & Fraser, *Biochem. J.* 283:1–19 (1992)). In the case of the glucagon/calcitonin receptor subfamily, relatedness based on sequence identity is apparent despite the diversity of the peptides that bind to these receptors (Attwood & Findlay, *Protein Eng.* 7:195–203 (1994)).

The structural features required for ligand binding and receptor activation have been investigated and found to vary according to ligand and receptor subfamily (Coughlin, *Curr. Opin. in Cell Biol.* 6:191–197 (1994)). Many small ligands such as 11-cis-retinal, serotonin, and acetylcholine, bind within the cavity formed by the receptors' transmembrane domains (Baldwin, *Curr. Opin. in Cell Biol.* 6:180–190 (1994); Dohlman, et al., *Annu. Rev. Biochem.* 283:1–19 (1992); and Savarese & Fraser, *Biochem. J.* 283:1–19 (1992)). Other ligands such as peptides and glycoprotein hormones require amino-terminal exodomains and most likely some portion of the extracellular loops for binding, but signaling requires the seven membrane spans (Holtmann, et al., *J. Biol. Chem.* 270:14394–14398 (1995) and Nagayama, et al., *Proc. Nat'l Acad. Sci. (USA)* 88:902–905 (1991)). A remarkable signaling mechanism has been described for the thrombin receptor in which thrombin cleaves its receptor's amino-terminal extension to create a new receptor amino terminus that functions as a tethered ligand and activates the receptor through interactions with the interhelical pocket (Vu, et al., *Cell* 64:1057–1068 (1991)).

Hamann, et al. (*J. Immunol.* 155:1942–1950 (1995)) report the isolation of a glycoprotein designated CD97. Seven hydrophobic segments within CD97 suggest that this glycoprotein is a 7TM molecule. CD97 is induced on the surface of most leukocytes upon activation. In its mature form, Hamann, et al. indicate that CD97 is a single chain glycoprotein of 722 amino acids in length with a molecular weight of 75 to 85 kDa.

SUMMARY OF THE INVENTION

The present invention relates to the previously unrecognized a subunit of CD97. The α subunit binds to the β subunit of CD97 to form an αβ heterodimer. The α subunit is localized extracellularly on T-cells. Upon activation, expression of the α subunit is dramatically increased and shed into the external medium. The α subunit plays a role in angiogenesis, inflammation, and atherosclerosis. Detection and inhibition of α subunit expression provides diagnostic and therapeutic methods for these disease states.

In one aspect, the present invention relates to an isolated protein comprising a soluble CD97 α subunit. The soluble CD97 α subunit is selected from the group consisting of α1, α2, and α3. The α1, α2 and α3 subunits are related in that they all originate as a proprotein with the β subunit (FIG. 1)

and are processed in the endoplasmic reticulum or early golgi to a specific α subunit with an identifying number of EGF repeats and a non-covalently linked β subunit.

The α3 subunit has a molecular weight of about 45 kDa in non-glycosylated form, has an EGF-like repeat selected from the group consisting of EGF-1 (SEQ ID NO:1), EGF-2 (SEQ ID NO:2), and EGF-5 (SEQ ID NO:5), and is immunologically cross-reactive to an antibody that is specifically reactive to the protein of SEQ ID NO:6. The α2 subunit has a molecular weight of about 50 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6. The α1 subunit has a molecular weight of about 55 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6. In some embodiments the α1 subunit further comprises an EGF-like repeat selected from the group consisting of EGF-3 (SEQ ID NO:3), and EGF-4 (SEQ ID NO:4). In other embodiments the α2 subunit further comprises EGF-like repeat SEQ ID NO:3. Conveniently, the isolated protein is recombinantly produced.

In another aspect, the present invention relates to an isolated nucleic acid encoding a soluble CD97 α subunit protein. The CD97 α subunit protein is selected from the group consisting of α1, α2, and α3. The α3 subunit has a molecular weight of about 45 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6. The α2 subunit has a molecular weight of about 50 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6. The α1 subunit has a molecular weight of about 55 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6.

In some embodiments, the nucleic acid encodes a CD97 α subunit selected from the group consisting of α1 and α2, further comprising an EGF-like repeat selected from the group consisting of SEQ ID NO:3, and SEQ ID NO:4. In some embodiments the α2 subunit further comprises EGF-like repeat SEQ ID NO:3. In additional embodiments, the nucleic acid is operably linked in forward or reverse orientation to a promoter, either of which can be used to transfect a host cell.

In an additional aspect the present invention relates to an isolated mammalian protein comprising a soluble CD97 α subunit. The CD97 α subunit is an extracellular protein comprising at least 10 contiguous amino acids from the protein of SEQ ID NO:6, is increased at least five-fold upon maximal activation of a T-cell with a T-cell mitogen, and is immunologically cross-reactive to an antibody that is specifically reactive to the protein of SEQ ID NO:6.

In yet another aspect, the present invention relates to an isolated nucleic acid, encoding a soluble CD97 α subunit, of at least 25 nucleotides in length, wherein the CD97 α subunit is selected from the group consisting of α1 and α2.

The α2 subunit has a molecular weight of about 50 kDa in non-glycosylated form, has an EGF-like repeat selected from the group consisting of: SEQ ID NO:1, SEQ ID NO:2, and SEQ ID NO:5, and is immunologically cross-reactive to an antibody that is specifically reactive to the protein of SEQ ID NO:6. The α1 subunit has a molecular weight of about 55 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6. In this aspect, the nucleic acid specifically hybridizes, under stringent conditions, at least two-fold above background to a CD97 nucleic acid in a human genomic library.

In an additional aspect, the present invention relates to an antibody composition specifically reactive, under immunologically reactive conditions, to a soluble CD97 α subunit selected from the group consisting of α1 and α2. The α2 subunit has a molecular weight of about 50 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6. The α1 subunit has a molecular weight of about 55 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6. In some embodiments the antibody composition comprises at least three unique antibodies.

In a further aspect, the present invention relates to a method for determining the degree of inflammation at a site in a mammal. The method comprises the steps of contacting an antibody composition to a biological sample from the site, wherein the antibody composition is specifically reactive, under immunologically reactive conditions, to a soluble CD97 α subunit selected from the group consisting of α1, α2, and α3.

The α3 subunit has a molecular weight of about 45 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6. The α2 subunit has a molecular weight of about 50 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6. The α1 subunit has a molecular weight of about 55 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6.

In the method, the antibody composition is incubated with the biological fluid. under immunologically reactive conditions conducive to formation of an specific antibody:CD97 α subunit complex, wherein detection of the amount of the complex indicates the extent of inflammation at the site. In preferred embodiments, the biological sample is selected from the group consisting of blood, synovial fluid, and cerebrospinal fluid.

In yet another aspect, the present invention relates to a method for inhibiting angiogenesis associated with chronic inflammation in a mammal, comprising administering a therapeutically effective amount of a CD97 antagonist selected from the group consisting of CD97 subunit antisense nucleic acid, CD97 subunit α decoy protein, and anti-CD97 α subunit antibody, wherein the CD97-subunit is selected from the group consisting of α1, α2, α3 and β. Subunits α3, α2, and α1 are as provided supra. The β subunit has a molecular weight of about 28 kDa as an unglycosylated protein and is immunologically crossreactive to an antibody that is specifically reactive to the protein of SEQ ID NO:6. The therapeutically effective amount is administered topically or parenterally.

In a further aspect, the present invention relates to a method of treating or inhibiting CD97 associated inflammation in a mammal, comprising administering a therapeutically effective amount of a CD97 antagonist selected from the group consisting of CD97 subunit antisense nucleic acid, CD97 subunit α decoy protein, and anti-CD97 subunit antibody, and wherein the CD97-subunit is selected from the group consisting of α1, α2, and α3. Subunits α3, α2, and α1 are as provided supra.

In yet another aspect, the present invention relates to a method for inhibiting atherosclerosis, comprising administering a therapeutically effective amount of a CD97 antagonist selected from the group consisting of CD97 subunit antisense nucleic acid, CD97 subunit α decoy protein, and anti-CD97 α subunit antibody, wherein the CD97-subunit is selected from the group consisting of α1, α2, α3 and β. Subunits α3, α2, α1, and β are as provided supra. The therapeutically effective amount is administered topically or parenterally.

In a further aspect, the present invention relates to a method for identifying a compound which inhibits soluble CD97 α subunit expression. The method comprises contacting, under cell culture conditions, the compound with a resting T-cell and an effective amount of a T-cell mitogen. In the method the compound is present in at least nanomolar concentrations. Changes in the expression level of the CD97 α subunit are assayed for, wherein the subunit is selected from the group consisting of α1, α2, and α3. Subunits α3, α2, and α1 are as provided supra. A reduced level of expression of the subunit relative to a negative control identifies the compound as an inhibitor. In preferred embodiments, the T-cell mitogen is selected from the group consisting of phytohemagglutinin, concanavalin A, phorbol 12-myristate 13-acetate, and pokeweed mitogen. Typically, changes in the expression of the CD97 α subunit are determined by immunoassay or nucleic acid assay.

BRIEF DESCRIPTION OF THE FIGURES

FIG. 1 shows the structure of the three isoforms of CD97 (nucleic acid=SEQ ID NO:8; amino acid=SEQ ID NO:6. The seven transmembrane domains are underlined; the signal sequence is underlined and italicized; the RGD sequence is boxed; the EGF-like repeats are boxed (SEQ ID NOS:1–5) and the EGF-like repeats contained in the larger isoforms are shaded, and potential N-linked glycosylation sites are within diamonds.

FIG. 3 shows a comparison of conserved motifs in CD97 (SEQ ID NOS:1–5), EMR1 (SEQ ID NO:20) and fibrillin (SEQ ID NO:19). The five EGF-like repeats encoded by full-length pAT276 are related to the EGF-like repeats in EMR1 and to those in fibrillin E/N β hydroxylation consensus=SEQ ID NO:21.

DETAILED DESCRIPTION OF THE INVENTION

Figure 2:
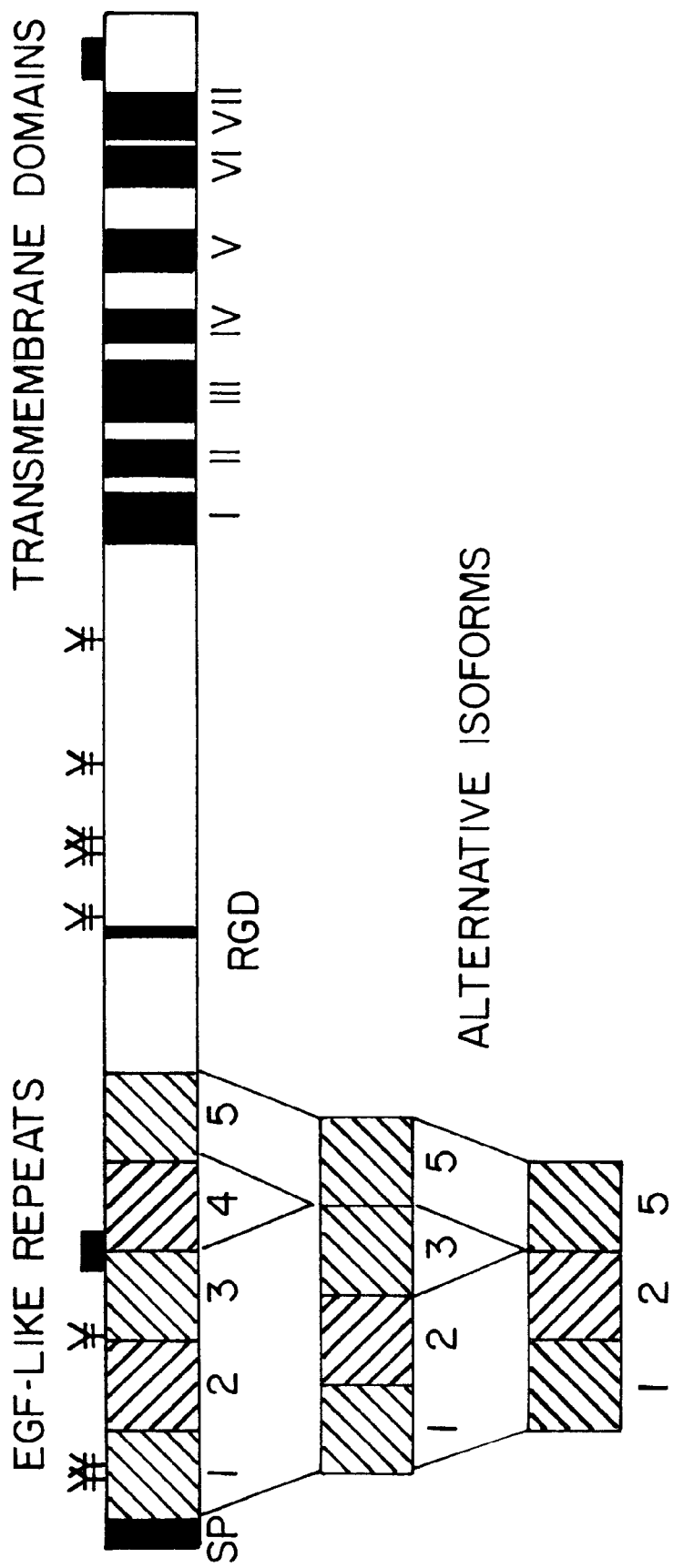
FIG. 2 shows the structure of the CD97 proprotein and subsequent processing to form the α subunits and β subunit. The transmembrane domains of the β subunit are shaded and numbered with Roman numerals. The signal peptide is labeled SP, The RGD sequence is noted and the alternative α subunit isoforms are indicated. Potential N-linked glycosylation sites are indicated by ¥, and the sequences used to develop antibodies against EGF3 and the carboxyl terminus are indicated by the filled rectangles.

The present invention provides compositions and methods directed to isolated α subunits of the 7TM protein CD97. Mature CD97 is not a monomeric chain. Instead, CD97 is a heterodimer existing in three isoforms—three forms of α subunit, and one invariant β subunit. The α subunit is an extracellular protein associated with the transmembrane β subunit. Upon activation of T-cells, the α subunit is dramatically upregulated and shed into the extracellular milieu. Thus CD97 α is a soluble protein. Extracellular CD97 α in resting T cells is present at about 1% of the induced level, whereas the difference between resting and induced levels of CD97 β is less than two-fold different.

The CD97 α proteins are found in tissues and body fluids surrounding sites of inflammation. CD97 α subunits act in the establishment and maintenance of inflammation. Soluble CD97 acts as an adhesion factor for endothelial cells and smooth muscle cells, implicating it as a modulator of atherosclerosis. Furthermore, CD97 α acts as a motility factor to cells bearing the $α_vβ_3$ receptor, indicative of its role in angiogenesis. Accordingly, the present invention provides methods to detect and inhibit inflammation, atherosclerosis, and angiogenesis associated with CD97 induction in mammalian cells. The compositions and methods have in vitro utility in the construction of proteins and subsequences thereof for the construction of antibodies, and nucleic acids and subsequences thereof for use as probes.

I. Definitions

Units, prefixes, and symbols can be denoted in their SI accepted form. Numeric ranges are inclusive of the numbers defining the range. Unless otherwise indicated, nucleic acids are written left to right in 5' to 3' orientation; amino acid sequences are written left to right in amino to carboxyl orientation, respectively. The headings provided herein are not limitations of the various aspects or embodiments of the invention which can be had by reference to the specification as a whole. Accordingly, the terms defined immediately below are more fully defined by reference to the specification as a whole.

As used herein, "angiogenesis associated with chronic inflammation" includes reference to disorders persisting for more than about a month in which a localized inflammation promotes angiogenesis.

As used herein, "antibody composition" includes reference to at least one antibody. In turn, "antibody" includes reference to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g. Fab', F(ab')$_2$, Fab, Fv, rIgG, and, inverted IgG). See, Pierce Catalog and Handbook, 1994–1995 (Pierce Chemical Co., Rockford, Ill.). An antibody immunologically reactive with a particular antigen can be generated in vivo or by recombinant methods such as selection of libraries of recombinant antibodies in phage or similar vectors. See, e.g., Huse, et al., *Science* 246:1275–1281 (1989); Ward, et al., *Nature* 341:544–546 (1989); and Vaughan, et al., *Nature Biotech.* 14:309–314 (1996).

As used herein, "antibody:CD97 α subunit complex" includes reference to a non-covalent, physical association, under the referenced conditions, between an antibody specifically reactive to a CD97 α subunit and a CD97 α subunit. The affinity constant of the antibody binding site for its cognate monovalent antigen is at least $10^7$, usually at least $10^8$, preferably at least $10^9$, more preferably at least $10^{10}$, and most preferably at least $10^{11}$ liters/mole.

As used herein, "antisense" includes reference to a single stranded nucleic acid sequence which selectively hybridizes, under selective hybridization conditions, to a single-stranded "sense" nucleic acid. Generally, the sense nucleic acid is, or is processed to, messenger RNA. Translation of the mRNA is interfered with by the antisense nucleic acid resulting in a measurable decrease in the level of protein encoded by the mRNA. An antisense nucleic acid can be produced in vivo by expressing the gene (or a gene subsequence) in reversed orientation such that the antisense strand is transcribed instead of the sense strand.

As used herein, the term "atherosclerosis" refers to a disease in which the inner arterial wall thickens due to the formation of plaques consisting of lipoproteins, dying blood cells, cholesterol and sometimes calcium.

As used herein, "biological sample" includes reference to a cell (e.g. T-cell), tissue (e.g., skin, smooth muscle or epithelial cells of the vascular system), or a fluid specimen. The fluid specimen may comprise cells or be cell-free and includes urine, blood, plasma, synovial fluid, cerebrospinal fluid, and sputum. Biological samples may also include sections of tissues such as frozen sections taken for histological purposes.

As used herein, "CD97 α subunit" or "soluble CD97 α subunit" includes reference to a protein present on the surface of T-cells which is upregulated upon activation of T-cells with a T-cell mitogen, and cross-reacts to antibodies elicited to an immunogen of SEQ ID NO:6. In preferred embodiments, the CD97 α subunit comprises at least one, preferably two, and more preferably three EGF-like repeat selected from the group consisting of (SEQ ID NO:1), (SEQ ID NO:2), and (SEQ ID NO:5). The CD97 α subunit can be shed from the surface of T-cells and found in solubilized form in the extracellular medium.

As used herein, "CD97 nucleic acid" includes reference to a nucleic acid encoding a protein comprising an amino acid sequence of a CD97 α subunit or CD97 α subunit subsequence of at least 10 contiguous amino acids.

As used herein, "cell culture conditions" includes reference to conditions which are conducive to replication of the referenced cell.

As used herein, "complementary" with respect to two referenced nucleic acid sequences includes reference to standard purine:pyrimidine (e.g., G:C, A:T) base-pairing between the referenced sequences. Unless otherwise stated, each of the nucleotides of the specified sequences is base-paired in complementary sequences.

As used herein, "contacting" includes reference to placement in direct physical association.

As used herein, "contiguous" in reference to a specified number of amino acid residues or nucleotides, includes reference to a sequence of amino acids or nucleotides, respectively, of the specified number from within the specified reference sequence which has the identical order of amino acids or nucleotides and the same adjacent amino acids or nucleotides as in the reference sequence.

As used herein, the term "decoy protein" includes reference to a functionally inactive protein which competes with a functionally active protein and thereby inhibits the activity promoted by the active protein. A CD97 α decoy protein can thus acts as a competitive inhibitor to native CD97 α.

As used herein, determination of the "degree of inflammation at a site in a mammal" includes reference to determining directly or indirectly the concentration of activated T-cells at the referenced site.

The terms "effective amount" or "amount effective to" or "therapeutically effective amount" includes reference to a dosage sufficient to produce a desired result such as inhibition of inflammation, atherosclerosis or angiogenesis.

As used herein, "effective amount of a T-cell mitogen" includes reference to an amount of mitogen which, in the appropriate culture medium, is sufficient to activate resting T-cells such that they enter the cell cycle. Exemplary T-cell mitogens include phytohemagglutinin (PHA), phorbol 13-myristate 12-acetate (PMA), pokeweed mitogen (PWM), and concanavalin A (ConA).

As used herein, "EGF-like repeat" includes reference to at least one of the sequences selected from the group consisting of SEQ ID NOs:1 through 5.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum,* or the ciliate Macronucleus, may be used when the nucleic acid is expressed in using the translational machinery of these organisms.

As used herein, "expression vector" includes reference to a nucleic acid construct, generated recombinantly or synthetically, which comprises a series of specified nucleic acid elements which permit transcription of a particular nucleic acid in a host cell. The expression vector can be part of a plasmid, virus, or nucleic acid fragment. Typically, the expression vector includes a nucleic acid to be transcribed, and a promoter.

As used herein, "host cell" includes reference to a cell which contains an expression vector and supports the replication or expression of the expression vector. Host cells may be prokaryotic cells such as *E. coli,* or eukaryotic cells such as yeast, insect, amphibian, or mammalian cells.

As used herein, "human genomic library" includes reference to a collection of isolated DNA molecules which substantially represent the entire genome of a human. Construction of genomic libraries is taught in standard molecular biology references such as Berger & Kimmel, *Guide to Molecular Cloning Techniques:* Methods in Enzymology, vol. 152, Academic Press, Inc., San Diego, Calif. (Berger); Sambrook et al., Molecular Cloning—A Laboratory Manual (2nd ed.) Vol. 1–3 (1989) (Sambrook, et al.); and Current Protocols in Molecular Biology, F. M. Ausubel et al., eds., Current Protocols, a joint venture between Greene Publishing Associates, Inc. and John Wiley & Sons, Inc., (1994 Supplement) (Ausubel).

As used herein, the term "immune-mediated angiogenesis" refers to neovascularization of sites of inflammation due to the influx of immune cells to the site of inflammation.

As used herein, "immunologically cross-reactive" or "immunologically reactive" includes reference to an antigen which is specifically reactive with an antibody which was generated using the same ("immunologically reactive) or different ("immunologically cross-reactive") antigen. Generally, the antigen is a CD97 protein, more typically a CD97 α subunit or subsequence thereof.

As used herein, "immunologically reactive conditions" includes reference to conditions which allow an antibody, generated to a particular epitope of an antigen, to bind to that epitope to a detectably greater degree than the antibody binds to substantially all other epitopes, generally at least two times above background binding, preferably at least five times above background. Immunologically reactive conditions are dependent upon the format of the antibody binding reaction and typically are those utilized in immunoassay protocols. See, Harlow & Lane, Antibodies, A Laboratory Manual, Cold Spring Harbor Publications, New York (1988) (Harlow & Lane) for a description of immunoassay formats and conditions.

As used herein, "increased upon activation of T-cells with a T-cell mitogen" includes reference to an increase in expression of the referenced protein upon activation of T-cells with an effective amount of a T-cell mitogen.

As used herein, "incubating" includes reference to a period of time sufficient for an energetically favorable reaction to proceed to a degree sufficient for the reaction to be detectable above background.

As used herein, "isoformn" includes reference to a family of functionally related proteins that differ in their amino acid sequences but are derived from the same nuclear transcript.

As used herein, "isolated" includes reference to material which is substantially or essentially free from components which normally accompany or interact with it as found in its naturally occurring environment. The isolated material optionally comprises material not found with the material in its natural environment.

As used herein, "mammal" includes reference to rats, mice, cats, dogs, cows, pigs, rabbits, and primates. Exemplary primates include monkeys, chimpanzees, and humans.

As used herein, "maximal activation" or "maximally activated" with respect to activation of a T-cell includes reference to the asymptotic level of activation that is approached using increasing amounts of a T-cell mitogen.

As used herein, "nucleic acid" includes reference to a deoxyribonucleotide or ribonucleotide polymer in either single- or double-stranded form, and unless otherwise stated, encompasses known analogues of natural nucleotides that hybridize to nucleic acids in a manner similar to naturally occurring nucleotides. Unless otherwise indicated, a particular nucleic acid sequence includes the complementary sequence thereof.

As used herein, "non-glycosylated form" includes reference to a protein which lacks sugar residues.

The term "operably linked to a promoter" refers to a functional linkage between a promoter and a second sequence, wherein the promoter sequence initiates and mediates transcription of the DNA sequence corresponding to the second sequence. Generally, operably linked to a promoter means that the nucleic acid sequences being linked are contiguous and, where necessary to join two protein coding regions, contiguous and in the same reading frame.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers.

The amino acids and analogs referred to herein are described by shorthand designations described in Table I:

TABLE I

Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | H |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Those of ordinary skill will readily understand that CD97 proteins of the present invention embrace minor variants of the CD97 α subunits. Accordingly, the present invention embraces conservatively modified variants of the CD97 α subunits and substantially similar variants of CD97 α subunits. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
See also, Creighton, Proteins, W. H. Freeman and Company (1984).

One of ordinary skill will recognize that individual substitutions, deletions or additions to a protein sequence which alters, adds or deletes a single amino acid or a small percentage of amino acids in the encoded sequence is a "conservatively modified variant" where the alteration results in the substitution of an amino acid with a chemically similar amino acid.

The terms "substantially similar" in the context of a peptide indicates that a peptide comprises a sequence with at least 90%, preferably at least 95% sequence identity to the reference sequence over a comparison window of 100 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

In turn, "sequence identity" in the context of two nucleic acid or polypeptide sequences includes reference to the nucleotides (or residues) in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a fill mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers & Miller, *Computer Applic. Biol. Sci.*, 4:11–17 (1988), e.g., as implemented in the program PC/GENE (Intelligenetics, Mountain View, Calif., USA). An indication that two peptide sequences are substantially similar is that one peptide is immunologically reactive with antibodies raised against the second peptide. Thus, a peptide is substantially similar to a second peptide, for example, where the two peptides differ only by a conservative substitution.

A "comparison window", as used herein, includes reference to a segment of about 100 residues in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith & Waterman, *Adv. Appl. Math.* 2:482 (1981); by the homology alignment algorithm of Needleman & Wunsch, *J. Mol. Biol.* 48:443 (1970); by the search for similarity method of Pearson & Lipman, *Proc. Nat'l Acad. Sci. USA* 85:2444 (1988); and by computerized implementations of these algorithms (including, but not limited to CLUSTAL in the PC/Gene program, GAP, BESTFIT, BLAST, FASTA, and TFASTA in the Wisconsin Genetics Software Package, Genetics Computer Group (GCG), 575 Science Dr., Madison, Wis., USA). The CLUSTAL program is well described by Higgins & Sharp, *Gene* 73:237–244 (1988); Higgins & Sharp, *CABIOS* 5:151–153 (1989); Corpet, et al., *Nucl. Acids Res.* 16:10881–90 (1988); Huang, et al., *Computer Applic. Biol. Sci.* 8:155–65 (1992); and Pearson, et al., *Methods in Molec. Biol.* 24:307–31 (1994).

As used herein, "promoter" includes reference to a nucleotide sequence which is recognized and bound by an RNA polymerase and which promotes transcription of a particular DNA sequence.

As used herein, "recombinant" includes reference to a protein produced using cells that do not have in their native form an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, "resting T cell" includes reference to a T-cell which is not passing through the cell-cycle. Cells under cell cycle arrest are sometimes said to be in $G_0$ phase.

As used herein, "selectively hybridizing" or "selective hybridization" or "selectively hybridizes" includes reference to hybridization, under stringent hybridization conditions, of a nucleic acid sequence to a specified nucleic acid target sequence to a detectably greater degree than its hybridization to non-target nucleic acid sequences and/or to the substantial exclusion of non-target nucleic acids. Selective hybridization yields a signal at least two, preferably three, more preferably four, and most preferably at least five-fold higher than background signal.

As used herein, "site" includes reference to a physiological area within the mammal. Generally, the site will be an area of inflammation due to the presence of a localized antigen.

As used herein, "specifically reactive" includes reference to the preferential association of a ligand, in whole or part, with a particular target molecule (i.e., "binding partner" or "binding moiety") relative to compositions lacking that target molecule. It is, of course, recognized that a certain degree of non-specific interaction may occur between a ligand and a non-target molecule. Nevertheless, specific binding, may be distinguished as mediated through specific recognition of the target molecule. Typically, specific binding results in a much stronger association between the ligand and the target molecule than between the ligand and non-target molecule. Specific binding by an antibody to a protein under such conditions requires an antibody that is selected for its specificity for a particular protein. The affinity constant of the antibody binding site for its cognate monovalent antigen is at least $10^7$, usually at least $10^8$, preferably at least $10^9$, more preferably at least $10^{10}$, and most preferably at least $10^{11}$ liters/mole. A variety of immunoassay formats are appropriate for selecting antibodies specifically reactive with a particular protein. For example, solid-phase ELISA immunoassays are routinely used to select monoclonal antibodies specifically reactive with a protein. See Harlow & Lane, supra, for a description of immunoassay formats and conditions that can be used to determine specific reactivity.

As used herein, "stringent conditions" includes reference to conditions under which a probe will preferentially hybridize to its target sequence and/or hybridize to its target sequence to the substantial exclusion of non-target sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. (As the target sequences are generally present in excess, at $T_m$ 50% of the probes are occupied at equilibrium). Typically, stringent conditions will be those in which the salt concentration is less than about 1.0 M Na$^+$, typically about 0.01 to 1.0 M Na$^+$ concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C. "Stringent hybridization conditions" or "stringent conditions" in the context of nucleic acid hybridization assay formats are sequence dependent, and are different under different environmental parameters. An extensive guide to the hybridization of nucleic acids is found in Tijssen, Laboratory Techniques in Biochemistry and Molecular Biology—Hybridization with Nucleic Acid Probes Part I, Chapter 2 "Overview of principles of hybridization and the strategy of nucleic acid probe assays", Elsevier, N.Y. (1993).

As used herein, "transfect" includes reference to the introduction of a nucleic acid into a eukaryotic cell where the nucleic acid may be incorporated into the genome of the cell (i.e., chromosome, plasmid, or mitochondrial DNA), converted into an autonomous replicon, or transiently expressed (e.g., transfected mRNA). The transfection can be in vivo or ex vivo. "Ex vivo transfection" means that transfection occurs outside the body of the mammal from which a cell or cells are obtained or from which a cell line is isolated. Ex vivo transfection is preferably followed by re-infusion of the transfected cells back into the organism. In contrast, by "in vivo transfection" is meant transfection occurs within the body of the specified mammal.

As used herein, "unique" with regard to antibodies includes reference to the antigen binding of the antibodies. The antigen binding site of unique antibodies in a composition are specifically reactive, under immunologically reactive conditions, to different epitopes.

II. Soluble CD97 Proteins

The present invention provides isolated proteins (CD97 proteins) comprising a mammalian CD97 α subunit and subsequences thereof. These isolated CD97 proteins are N amino acid residues in length, where N is any one of the integers selected from the group consisting of from about 50 to 850. Generally, the isolated proteins comprising a mammalian CD97 α subunit are less than about 800 amino acids in length, preferably less than 700 amino acids in length, more preferably less than 600 amino acids in length, and most preferably less than about 500 amino acids in length, but at least about 50 amino acids in length. Thus, the present invention provides isolated, mature (i.e., processed) CD97 α subunit proteins, CD97 pre-proteins (i.e., pre-processed), and subsequences thereof. Subsequences of the CD97 α subunit can be used as an immunogen to elicit the production of anti-CD97 α subunit antibodies. These antibodies can be used as immunodiagnostic probes for assessing increased or decreased expression of CD97 α subunit proteins in drug screening assays (e.g., for anti-inflammatory drugs). Alternatively, antibodies can be used to interfere with angiogenesis, atherosclerosis or in the inflammatory cascade in which CD97 α plays a role.

Isolated mammalian proteins comprising a soluble CD97 α subunit comprise at least 10 contiguous amino acids, preferably at least 15 contiguous amino acids, more preferably at least 20 contiguous amino acids, and most preferably at least 25, 30, 35, or 40 contiguous amino acids from SEQ ID NO:6. The isolated mammalian protein is immunologically cross-reactive to an antibody composition that is generated from (e.g., screened, synthesized, or elicited) and specifically reactive to a protein immunogen of SEQ ID NO:6. Generally, the isolated mammalian protein will be immunologically cross-reactive to an antibody composition that is specifically reactive to a human CD97 α subunit selected from the group consisting of α1, α2, and α3 but not immunologically cross-reactive to a human CD97 β subunit. Accordingly, in preferred embodiments, the contiguous amino acids will be from within any of the first 400 amino acids from the amino terminus of SEQ ID NO:6, preferably within any of the first 375, more preferably with any of the first 350 amino acids from the amino terminus of SEQ ID NO:6. In general, the CD97 α subunit will be immunologically cross-reactive to an antibody composition that is specifically reactive to at least one epitope within the first 400, 375, or 350 amino acids from the amino terminus of SEQ ID NO:6 but is not cross reactive to a subsequence of SEQ ID NO:6 which is lacking one of these regions.

The immunological cross-reactivity of the isolated mammalian proteins of the present invention to SEQ ID NO:6 provides a means to isolate soluble CD97 α from various mammalian species. Expression of the soluble CD97 α subunit can be induced by administering an antigen to a localized site in a mammal to promote inflammation. Antigens to promote inflammation are well known in the art. A cell-free fluid sample can be obtained from the site of inflammation. For example, skin infiltrate or synovial fluid from the site of inflammation can be obtained and filtered or otherwise treated to remove cells. Since activated T-cells shed the CD97 α subunit into extracellular milieu, CD97 α can be specifically isolated from the cell-free biological fluid using an antibody composition (e.g., in an immunoaffinity column) which is generated against and specifically reactive, under immunologically reactive conditions, to the protein of SEQ ID NO:6. In a particularly preferred method, the antibody composition which is generated against the protein of SEQ ID NO:6 is fully immunosorbed against EGF-like repeats 1 through 5 (SEQ ID NOs:1–5), or a region corresponding to about amino acid 22 through about amino acid 257 of SEQ ID NO:6, to remove anti-EGF-like repeat antibodies in the composition. The immunosorbed antibody composition can be used to avoid cross-reaction and isolation of non-CD97 mammalian proteins comprising EGF-like repeats having substantially similar antigenic determinants to EGF-like repeats 1 through 5. Preferably, the antibody composition is a polyclonal antibody composition.

The mammalian protein may be isolated from any number of mammals including: rat, mice, cattle, dog, pig, guinea pig, or rabbit, and most preferably a primate such as macaques, chimpanzees, or humans. Generally, the amount of the CD97 α subunit expressed by the cell can be increased to a level at least 3-fold greater than in resting T-cells by activation with a T-cell mitogen, generally at least 4-fold, preferably at least 6-fold, and more preferably at least 8-fold greater than in resting T-cells. The isolated mammalian proteins of the invention can comprise at least one, two, three, four, or five EGF-like repeats where the EGF-like repeats are selected from the group consisting of SEQ ID NO:1, SEQ ID NO:2, SEQ ID NO:3, SEQ ID NO:4, SEQ ID NO:5, and conservatively modified variants thereof. In some embodiments, the CD97 α subunit will comprise the RGD binding motif: Arg-Gly-Asp (SEQ ID NO:7).

Isolated mammalian CD97 proteins of the present include those proteins comprising at least N contiguous amino acids from a human CD97 α subunit selected from the group consisting of α1, α2, and α3, where N is any integer selected from the group consisting of from 10 to 300. Generally, the isolated proteins comprise at least 100 contiguous amino acids of a CD97 α subunit, typically at least 150 contiguous amino acids, usually at least 200 contiguous amino acids, preferably at least 250 contiguous amino acids, more preferably at least 300 contiguous amino acids, and most preferably the full-length sequence of the native, mature form of the CD97 α subunit of interest. The mature form of the CD97 α subunit is an extracellular protein noncovalently associated with the CD97 β subunit. The mature form of the CD97 α subunit is formed from a pre-protein which is subsequently processed into mature CD97 α and β subunits.

The human CD97 α1 subunit is a T-cell protein having a molecular weight of about 55 kDa (kilodaltons) as an unglycosylated protein. Full-length human CD97 α1 has five different EGF-like repeats of SEQ ID NOs:1, 2, 3, 4, and 5. Generally, the isolated proteins comprising a CD97 α1 subunit of the present invention will comprise at least one EGF-like repeat, and preferably at least two, three, four, or five different EGF-like repeats from the group consisting of SEQ ID NOs:1, 2, 3, 4, and 5. CD97 α subunits, including subunits α1, α2, and α3, typically comprise the binding motif Arg-Gly-Asp (SEQ ID NO:7).

The human CD97 α2 subunit is a T-cell protein having a molecular weight of about 50 kDa as an unglycosylated protein. Full length human CD97 α2 has four different EGF-like repeats of SEQ ID NOs: 1, 2, 3, and 5. The isolated proteins comprising a CD97 α2 subunit of the present invention will comprise at least one EGF-like repeat, and preferably at least two, three, or four, different EGF-like repeats from the group consisting of SEQ ID NOs:1,2,3, and 5.

The CD97 α3 subunit is a T-cell protein having a molecular weight of about 45 kDa in non-glycosylated form. Full length human CD97 α3 has three different EGF-like repeats of SEQ ID NOs:1, 2, and 5. The isolated proteins comprising a CD97 α3 subunit of the present invention will comprise at least one EGF-like repeat, and preferably at least two, or three different EGF-like repeats from the group consisting of SEQ ID NOs: 1, 2, and 5.

Steady state levels of CD97 α subunits are increased at least two-fold, usually five-fold, and usually at least 10-fold in maximally activated T-cells relative to resting T-cells. Maximal activation includes reference to an amount of a T-cell mitogen which is not rate-limiting with respect to driving a resting T-cell through the cell cycle. In vitro activation of T-cells is known in the art. See, e.g., Example 5.

The isolated CD97 proteins of the present invention may comprise an amino acid sequence coding for the CD97 β subunit. The native CD97 β subunit is an integral membrane protein. Typically, CD97 β has a molecular weight of about 28 kDa as an unglycosylated protein. The CD97 β subunit is immunologically cross-reactive to an antibody composition that is specifically reactive to the protein of SEQ ID NO:6. Accordingly, proteins comprising mammalian CD97 α and/ or CD97 β subunits can be identified using antibodies generated to antigenic regions of SEQ ID NO:6. As those of ordinary skill will readily understand, antigenic regions are preferably derived from extracellular regions of SEQ ID NO:6. Thus, a subsequence of CD97 comprising at least one EGF-like repeat selected from the group consisting of SEQ ID NOs:1 through 5, and the intracytoplasmic carboxyl tail are particularly preferred antigens to generate anti-CD97 antibodies. Antibodies specifically reactive to a CD97 β subunit are preferably generated using the region of CD97 which is localized intracellularly in the mature form of the CD97 protein (e.g., carboxyl terminal proximal to the membrane spanning helices of SEQ ID NO:6). Antibodies specifically reactive to the CD97 α subunit are generated using the region of CD97 which is amino terminal proximal to an RGD (Arg-Gly-Asp) sequence (SEQ ID NO:7).

An embodiment of the proteins of the present invention comprises modifications to the N- and C-terminal residues. As will be well understood by the artisan, the N- and C-termini may be modified to alter physical or chemical properties of the peptide, such as, for example, to affect binding, stability, bioavailability, and the like.

Modifications of proteins with various amino acid mimetics or D-amino acids, for instance at the N- or C- termini, are useful for instance, in increasing the stability of the peptide in vivo. In one aspect, such peptides are synthesized as "inverso" or "retroinverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions more than compensate for a difference in affinity compared to the corresponding L-peptide. In a further aspect, L-amino acid containing proteins with or without substitutions are capped with a D-amino acid which inhibits exopeptidase destruction of the immunogenic peptide.

Stability is assayed in a number of ways. For instance, peptidases and various biological media, such as human plasma and serum, have been used to test stability. See, e.g., Verhoef, et al., *Eur. J. Drug Metab. Pharmacokin.* 11:291–302 (1986); Walter, et al., *Proc. Soc. Exp. Biol. Med.* 148:98–103 (1975); Witter, et al., *Neuroendocrinology* 30:377–381 (1980); Verhoef, et al., *J. Endocrinology* 110:557–562 (1986); Handa, et al., *Eur. J. Pharmacol.* 70:531–540 (1981); Bizzozero, et al., *Eur. J. Biochem.* 122:251–258 (1982); and Chang, *Eur. J. Biochem.* 151:217–224 (1985), all of which are incorporated herein by reference.

In another aspect of the invention, stability is also increased by introducing D-amino acid residues at the C- and N-termini of the peptide. Previous studies have indicated that the half-life of L-amino acid-containing peptides in vivo and in vitro, when incubated in serum-containing medium, are extended considerably by rendering the peptides resistant to exopeptidase activity by introducing D-amino acids at the C- and N-termini.

In one embodiment of the invention, the proteins or analogs of the invention are modified by altering the order or composition of certain residues, it being readily appreciated that certain amino acid residues essential for biological activity, e.g., those at critical contact sites, will generally not be altered without an adverse effect on biological activity. The non-critical amino acids need not be limited to those naturally occurring in proteins, such as L-α-amino acids, or their D-isomers, but will also include non-protein amino acids as well, such as β-γ-δ-amino acids, as well as many derivatives of L-α-amino acids. As discussed above, a protein of the present invention will generally comprise either L-amino acids or D-amino acids, but not D-amino acids within a core binding region.

The peptides of the invention are prepared in a wide variety of ways. In one aspect, the proteins are synthesized in solution or on a solid support in accordance with conventional techniques. Various automatic synthesizers are commercially available and can be used in accordance with known protocols. See, for example, Stewart and Young, *Solid Phase Peptide Synthesis,* 2d. Ed., Pierce Chemical Co. (1984), supra.

Alternatively, recombinant DNA technology is employed wherein a nucleotide sequence which encodes the protein of interest is inserted into an expression vector, transformed or transfected into an appropriate host cell and cultivated under conditions suitable for expression. These procedures are generally known in the art, as described generally in Sambrook, et al., *Molecular Cloning, A Laboratory Manual,* Cold Spring Harbor Press, Cold Spring Harbor, N.Y. (1989).

In another aspect, the coding sequence for soluble CD97 and its subunits contemplated herein are synthesized by chemical techniques, for example, the phosphotriester method of Matteucci, et al., *J. Am. Chem. Soc.* 103:3185 (1981). Modification is made by substituting the appropriate base(s) for those encoding the native peptide sequence. Nucleic acid sequences which encode for appropriate linkers are then be added to the CD97 coding sequence and ligated into expression vectors commonly available in the art, and the vectors used to transform suitable hosts to produce the desired CD97 peptide. A number of such vectors and suitable host systems are now available.

For expression of CD97, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence.

One of skill would recognize that modifications can be made to a CD97 protein without diminishing its biological activity. Some modifications are made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Once the nucleic acids encoding an isolated CD97 protein of the present invention are isolated and cloned, one may express the desired protein in recombinantly engineered cells such as bacteria, yeast, insect (especially employing baculoviral vectors), and mammalian cells.

A. Expression in Prokaryotes

Examples of regulatory regions suitable for this purpose in *E. coli* are the promoter and operator region of the *E. coli* tryptophan biosynthetic pathway as described by Yanofsky, *Bacteriol.* 158:1018–1024 (1984), and the leftward promoter of phage lambda ($P_L$) as described by Herskowitz & Hagen, *Ann. Rev. Genet.* 14:399–445 (1980). The inclusion of selection markers in DNA vectors transfected in *E. coli* is also useful. Examples of such markers include genes specifying resistance to ampicillin, tetracycline, or chloramphenicol. See, Sambrook, et al. for details concerning selection markers for use in *E. coli.*

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for CD97 proteins are available using *E. coli,* Bacillus sp. and Salmonella (Palva, et al., *Gene* 22:229–235 (1983); and Mosbach, et al., *Nature* 302:543–545 (1983)).

When expressing CD97 proteins in *S. typhimurium,* one should be aware of the inherent instability of plasmid vectors. To circumvent this, the foreign gene can be incorporated into a nonessential region of the host chromosome. This is achieved by first inserting the gene into a plasmid such that it is flanked by regions of DNA homologous to the insertion site in the Salmonella chromosome. After introduction of the plasmid into the *S. typhimurium,* the foreign gene is incorporated into the chromosome by homologous recombination between the flanking sequences and chromosomal DNA.

An example of how this can be achieved is based on the his operon of Salmonella. Two steps are involved in this process. First, a segment of the his operon must be deleted in the Salmonella strain selected as the carrier. Second, a plasmid carrying the deleted his region downstream of the gene encoding the CD97 protein is transfected into the his Salmonella strain. Integration of both the his sequences and a gene encoding a CD97 protein occurs, resulting in recombinant strains which can be selected as his$^+$.

Detection of the expressed protein is achieved by methods known in the art and include, for example, radioimmunoassays, Western blotting techniques or immunoprecipitation. Purification from *E. coli* can be achieved following procedures described in U.S. Pat. No. 4,511,503.

B. Expression in Eukaryotes

A variety of eukaryotic expression systems such as yeast, insect cell lines, bird, fish, frog, and mammalian cells, are known to those of skill in the art. As explained briefly below, the isolated proteins of the present invention may be expressed in these eukaryotic systems.

Synthesis of heterologous proteins in yeast is well known. Methods in Yeast Genetics, Sherman, F., et al., Cold Spring Harbor Laboratory, (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., *Gene* 8:17–24 (1979); and Broach, et al., *Gene* 8:121–133 (1979)).

Two procedures are used in transfecting yeast cells. In one procedure, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in Beggs, *Nature* 275:104–109 (1978); and Hinnen, et al., *Proc. Nat'l Acad. Sci. USA* 75:1929–1933 (1978). The second procedure does not involve removal of the cell wall. Instead the cells are treated with lithium chloride or acetate and PEG and put on selective plates (Ito, et al., *J. Bact.* 153:163–168 (1983)).

In a preferred aspect, CD97 proteins, once expressed, are isolated from yeast by lysing the cells and applying standard protein isolation techniques to the lysates. The monitoring of the purification process is accomplished by using western blot techniques or radioimmunoassay or other standard immunoassay techniques.

In a preferred embodiment, the sequences encoding CD97 proteins are ligated to various expression vectors for use in transfecting cell cultures of, for instance, mammalian, insect, bird, amphibian, or fish origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the CHO cell lines, and various human cells such as COS cell lines, HeLa cells, myeloma cell lines, and Jurkat cells. Expression vectors for these cells include expression if control sequences, such as an origin of replication, a promoter (e.g., the CMV promoter, a HSV tk promoter or pgk (phosphoglycerate kinase) promoter), an enhancer (Queen, et al., *Immunol. Rev.* 89:49 (1986)), and necessary processing information sites, such as ribosome binding sites, RNA splice sites, polyadenylation sites (e.g., an SV40 large T antigen poly(A+) addition site), and transcriptional terminator sequences. Other animal cells useful for production of CD97 proteins are available, for instance, from the American Type Culture Collection Catalogue of Cell Lines and Hybridomas (7th edition, 1992).

Appropriate vectors for expressing CD97 proteins in insect cells are usually derived from the SF9 baculovirus. Suitable insect cell lines include mosquito larvae, silkworm, armyworm, moth and Drosophila cell lines such as a Schneider cell line (See Schneider, *J. Embryol. Exp. Morphol.* 27:353–365 (1987).

As indicated above, the vector, e.g., a plasmid, which is used to transfect the host cell, preferably contains DNA sequences to initiate transcription and sequences to control the translation of the protein. These sequences are referred to as expression control sequences.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Optionally, sequences for accurate splicing of the transcript are also included. An example of a splicing sequence is the VP1 intron from SV40 (Sprague, et al., *J. Virol.* 45:773–781 (1983)).

Additionally, gene sequences to control replication in the host cell are incorporated into the vector such as those found in bovine papilloma virus type-vectors. Saveria-Campo, "Bovine Papilloma virus DNA a Eukaryotic Cloning Vector," DNA Cloning Vol. II: A Practical Approach, Glover, (ed.), IRL Press, Arlington, Va. pp. 213–238 (1985).

The host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells. The transfected cells are cultured by means well known in the art. See, Kuchler, Biochemical Methods in Cell Culture and Virology, Dowden, Hutchinson and Ross, Inc., (1977). The expressed proteins are recovered by well known mechanical, chemical or enzymatic means.

The CD97 proteins of the present invention which are produced by recombinant DNA technology are purified by standard techniques well known to those of skill in the art. Recombinantly produced CD97 proteins are directly expressed or expressed as a fusion protein. In a preferred embodiment, the recombinant CD97 protein is purified by a combination of cell lysis (e.g., sonication) and affinity chromatography. For fusion products, subsequent digestion of the fusion protein with an appropriate proteolytic enzyme releases the desired recombinant CD97 protein.

Alternatively, the CD97 proteins of this invention, recombinant or synthetic, are purified to substantial purity by standard techniques well known in the art, including selective precipitation with such substances as ammonium sulfate, column chromatography, immunopurification methods, and others. See, for instance, Scopes, Protein Purification: Principles and Practice, Springer-Verlag: New York (1982); and Deutscher, Guide to Protein Purification, Academic Press (1990).

III. Nucleic Acids Encoding CD97 Proteins

The present invention provides for isolated nucleic acids (CD97 nucleic acids) encoding a mammalian protein comprising a CD97 α subunit. Isolated mammalian CD97 proteins of the present invention are discussed more fully above. In preferred embodiments, the CD97 nucleic acid is shown as SEQ ID NO:8.

This invention also provides nucleic acid compositions and methods of detecting and/or quantifying CD97 protein expression by assaying for the gene transcript (e.g., nuclear RNA, mRNA) using nucleic acids coding for CD97 proteins. The assay is for the presence or absence of the normal gene or gene product, for the presence or absence of an abnormal gene or gene product, or quantification of the transcription levels of normal or abnormal CD97 gene product. Nucleic acid assays are well known in the art and included in standard molecular biology references such as those incorporated by reference herein.

For example, amongst the various hybridization formats well known to the skilled artisan are included solution phase, solid phase, mixed phase, or in situ hybridization assays. Briefly in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase hybridizations, nucleic acid intermediates in solution hybridize to target nucleic acids in solution as well as to a nucleic acid linked to a solid support. In in situ hybridization, the target nucleic acid is liberated from its cellular surroundings so that it is available for hybridization within the cell while preserving the cellular morphology for subsequent interpretation and analysis. The following articles provide an overview of the various hybridization assay formats: Singer, et al., *Biotechniques* 4(3):230–250 (1986); Haase, et al., Methods in Virology, Vol. VII, pp. 189–226 (1984); Wilkinson, "The theory and practice of in situ hybridization," In Situ Hybridization, Wilkinson. ed., IRL Press, Oxford University Press, Oxford; and Hames & Higgins, Nucleic Acid Hybridization: A Practical approach, S. J., IRL Press (1987).

Those of skill in the art will appreciate that various degrees of stringency of hybridization will be employed in the assay, and either the hybridization or the wash medium will be stringent. As the conditions for hybridization become more stringent, there must be a greater degree of complementarity between the probe and the target for duplex formation to occur. The degree of stringency is controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%.

The degree of complementarity (sequence identity) required for detectable binding will vary in accordance with the stringency of the hybridization medium and/or wash medium. The degree of complementarity will be optimally 100 percent; however, it should be understood that minor sequence variations in the probes and primers may be compensated for by reducing the stringency of the hybridization and/or wash medium as described below. Thus, despite the lack of 100% complementarity under reduced conditions of stringency, functional nucleic acids of the present invention having minor base differences from the CD97 nucleic acid targets are possible. Therefore under hybridization conditions of reduced stringency, it may be possible to construct an oligonucleotide having substantial identity to an oligonucleotide complementary to the target sequence while maintaining an acceptable degree of specificity. Substantial identity in the context of nucleic acids means that the two molecules hybridize to each other under stringent conditions. Generally, stringent conditions are selected to be about 5° C. to 20° C. lower than the thermal melting point ($T_m$) for the specific sequence at a defined ionic strength and pH. Typically, stringent conditions will be those in which the salt concentration is about 0.02 M at pH 7 and the temperature is at least about 60° C., more preferably 65° C.; however, for in situ hybridization the temperature is preferably 40° C. Stringent conditions typically include at least one wash in 0.2×SSC at a temperature of at least about 50° C., usually about 55° C. to about 60° C., for 20 minutes, or equivalent conditions. The hybridization format or buffers are not critical aspects of the present invention and those of skill will recognize that further advances, improvements, or modifications in nucleic acid hybridization, amplification, and detection are within the scope of the invention.

In one aspect of the invention, the nucleic acids of the present invention, whether derived from a biological source, artificially constructed or both, are operably linked to a promoter. Those of ordinary skill will recognize that a duplex CD97 nucleic acid operably linked to a promoter in forward orientation directs transcription of mRNA which is translated into a CD97 protein of the present invention. A duplex CD97 nucleic acid operably linked to a promoter in reverse orientation directs transcription of antisense mRNA. Antisense nucleic acids are used for probes in assays for normal or abnormal gene product or to quantitate the expression of mRNA coding for CD97 in, for example, drug assays or measurements of T-cell activation. Accordingly, the CD97 nucleic acids of the present invention are inclusive of both sense and antisense CD97 nucleic acids unless otherwise indicated.

Nucleic acids of the present invention are also used as probes, for example, in detecting deficiencies in the level of mRNA, mutations in the gene (e.g., substitutions, deletions, or additions), for monitoring upregulation of CD97 in drug screening assays, or for recombinant expression of CD97 proteins for use as immunogens in the preparation of antibodies. Isolated CD97 nucleic acids which are complementary (antisense) to endogenous CD97 mRNA can be used to modulate the level of endogenous CD97 protein in a mammalian cell.

The present invention also provides a CD97 α subunit protein encoded by a nucleic acid which is amplified using primers that selectively hybridize, under selective hybridization conditions, to SEQ ID NO:8 as well as oligonucleotides having the sequences ATGGGAGGC-CGCGTCTTTCTCGCATTCTGTGT (SEQ ID NO:7) and GGGCCCTCAGGGCATCAGAGTCCGGCATA (SEQ ID NO: 18).

The isolated nucleic acid compositions of this invention, whether RNA, cDNA, genomic DNA, or a hybrid of the various combinations, are isolated from biological sources or synthesized in vitro. As those of skill in the art will readily understand, one method of isolating nucleic acids encoding proteins comprising a CD97 α subunit is by screening mammalian nucleic acid libraries. Methods for constructing and screening libraries, such as a T-cell cDNA library or a genomic library, are well known in the art. Probes for screening will typically be at least 25, preferably at least 50, more preferably at least 100, and most preferably at least 150, 200, or 300 contiguous nucleotides from SEQ ID NO:8. Preferably, the probe will comprise the nucleic acid encoding the R-G-D sequence (SEQ ID NO:7). In particularly preferred embodiments, the probe selectively hybridizes, under stringent conditions, to the same sequence as an oligonucleotide of at least 25 nucleotides in length which is a subsequence from within the coding sequence of SEQ ID NO:8. As will be appreciated by the skilled artisan, the more evolutionarily distant the mammalian species is related to humans, the lower the hybridization stringency used for screening non-human mammalian libraries.

Deoxynucleotides encoding isolated proteins of the present invention can be prepared by any suitable method, including, for example, cloning and restriction of appropriate sequences as discussed supra, or by direct chemical synthesis by methods such as the phosphotriester method of Narang, et al., *Meth. Enzymol.* 68:90–99 (1979); the phosphodiester method of Brown, et al., *Meth. Enzymol.* 68:109–151 (1979); the diethylphosphoramidite method of Beaucage, et al., *Tetra. Lett.* 22:1859–1862 (1981); the solid phase phosphoramidite triester method described by Beaucage & Caruthers, *Tetra. Letts.* 22(20):1859–1862 (1981), for example using an automated synthesizer as described in Needham-VanDevanter, et al., *Nucl. Acids Res.* 12:6159–6168 (1984); and the solid support method of U.S. Pat. No. 4,458,066. Chemical synthesis produces a single stranded oligonucleotide. This is converted into double stranded DNA by methods known in the art including, hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences to form longer sequences.

In one embodiment, the isolated nucleic acids of the present invention are cloned by transfection into a host cell, or amplified by in vitro methods. Amplification methods include the polymerase chain reaction (PCR), the ligase chain reaction (LCR), the transcription-based amplification system (TAS), the self-sustained sequence replication system (SSR). A wide variety of cloning methods, host cells, and in vitro amplification methodologies are well-known to persons of skill.

For example, as those of skill are aware, the first step of each cycle of the PCR involves the separation of the nucleic acid duplex formed by the primer extension. Once the strands are separated, the next step involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid. In the preferred embodiment of the PCR process, strand separation is achieved by heating the reaction to a sufficiently high temperature for an sufficient time to cause the denaturation of the duplex but not to cause an irreversible denaturation of the polymerase (see U.S. Pat. No. 4,965,188). Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis.

Examples of techniques and instructions sufficient to direct persons of skill through many cloning exercises are found in Berger & Kimmel; Sambrook, et al.; Ausubel, et al.; Cashion, et al., U.S. Pat. No. 5,017,478; and Carr, European Patent No. 246,864. Cloning vectors and host cells are readily obtained through commercial sources or from the American Type Culture Collection.

Examples of techniques sufficient to direct persons of skill in in vitro amplification methods are found in Berger, Sambrook, and Ausubel, as well as Mullis, et al., U.S. Pat. No. 4,683,202; and Innis, et al.; Amnheim & Levinson *C&EN* 36–47 (Oct. 1, 1990); Kwoh, et al., *Proc. Nat'l Acad. Sci. USA* 86:1173 (1989); Guatelli, et al., *Proc. Nat'l Acad. Sci. USA* 87:1874 (1990); Lomell, et al., *J. Clin. Chem.* 35:1826 (1989); Landegren, et al. *Science* 241:1077–1080 (1988); Van Brunt, *Biotechnology* 8:291–294 (1990); Wu & Wallace, *Gene* 4:560 (1989); and Barringer, et al., *Gene* 89:117 (1990).

Where the nucleic acid encoding a CD97 protein is to be used as a nucleic acid probe, it is often desirable to label the nucleic acid with detectable labels. The labels are incorporated by any of a number of means well known to those of skill in the art. In one embodiment, the label is simultaneously incorporated during the amplification procedure in the preparation of the nucleic acids. Thus, for example, polymerase chain reaction (PCR) with labeled primers or labeled nucleotides provide a labeled amplification product. In another preferred embodiment, transcription amplification using a labeled nucleotide (e.g., fluorescein-labeled UTP and/or CTP) incorporates a label into the transcribed nucleic acids.

Alternatively, a label is added directly to an original nucleic acid sample (e.g., mRNA, poly(A)+ mRNA, cDNA, etc.) or to the amplification product after the amplification is completed. Means of attaching labels to nucleic acids are well known to those of skill in the art and include, for example nick translation or end-labeling (e.g., with a labeled RNA) by phosphorylation of the nucleic acid and subsequent attachment (ligation) of a nucleic acid linker joining the sample nucleic acid to a label (e.g., a fluorophore).

Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, Texas red, rhodamine, green fluorescent protein, and the like), radiolabels (e.g. $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels are detected using photographic film or scintillation counters, fluorescent markers are detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

IV. Antibody Composition to CD97 Proteins

The present invention provides antibody compositions comprising at least one antibody, wherein the composition is specifically reactive, under immunologically reactive conditions, to an isolated protein of the present invention. Antibodies are raised to the CD97 α subunit protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. In a further aspect of the invention, anti-idiotypic antibodies are also generated. In preferred embodiments, antibodies are constructed or elicited using a human CD97 α subunit as an immunogen. The human CD97 α subunit is selected from the group consisting of α1, α2, and α3.

Many methods of making antibodies are known to persons of skill. The following discussion is presented as a general overview of the techniques available; however, one of skill will recognize that many variations upon the following methods are known.

A. Antibody Production

A number of immunogens are used to produce antibodies immunologically reactive with a CD97 protein. An isolated recombinant, synthetic, or native CD97 protein of 5 contiguous amino acids in length or greater from SEQ ID NO:6 is the preferred immunogen (antigen) for the production of monoclonal or polyclonal antibodies. In one class of preferred embodiments, an immunogenic protein conjugate is also included as an immunogen. Naturally occurring CD97 proteins are also used either in pure or impure form.

The CD97 protein is then injected into an animal capable of producing antibodies. Either monoclonal or polyclonal antibodies can be generated for subsequent use in immunoassays to measure the presence and quantity of the CD97 protein. Methods of producing polyclonal antibodies are known to those of skill in the art. In brief, an immunogen (antigen), preferably a purified CD97 protein, a CD97 protein coupled to an appropriate carrier (e.g., GST, keyhole limpet hemanocyanin, etc.), or a CD97 protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by test bleeds and determining the titer of reactivity in the test bleed to the CD97 protein of interest. When appropriately high titers of antibody to the immunogen are obtained from the animal, blood is collected and antisera prepared. Further fractionation of the antisera to enrich for antibodies reactive to the CD97 protein is performed where desired (see, e.g., Coligan, Current Protocols in Immunology, Wiley/Greene, NY (1991); and Harlow & Lane).

Antibodies, including binding fragments and single chain recombinant versions thereof, against predetermined fragments of CD97 protein are raised by immunizing animals, e.g., with conjugates of the fragments with carrier proteins as described above. Typically, the immunogen of interest is a CD97 protein of at least about 5 amino acids, more typically the CD97 protein is at least 10 amino acids in length, preferably, at least 15 amino acids in length, more preferably at least 25 amino acids in length. In particularly preferred embodiments, the immunogen is derived from the extra- or intra-cytoplasmic region of the CD97 protein. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonal antibodies are screened for binding to a CD97 protein from which the immunogen was derived. Specific monoclonal and polyclonal antibodies will usually bind with an affinity constant of at least $10^{-7}$ M, preferably at least $10^{-8}$ M, preferably at least $10^{-9}$ M, more preferably at least $10^{-10}$ M, most preferably at least $10^{-11}$ M.

In some instances, it is desirable to prepare monoclonal antibodies from various mammalian hosts, such as mice, rodents, primates, humans, etc. Description of techniques for preparing such monoclonal antibodies are found in, e.g., Basic and Clinical Immunology (4th ed.), Stites et al.,(eds.), Lange Medical Publications, Los Altos, Calif., and references cited therein; Harlow & Lane; Goding, Monoclonal Antibodies: Principles and Practice (2d ed.) Academic Press, New York, N.Y. (1986); and Kohler & Milstein, *Nature* 256:495–497 (1975). Summarized briefly, this method proceeds by injecting an animal with an immunogen comprising a CD97 protein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transfection with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The CD97 proteins and antibodies of the present invention are used with or without modification, and include chimeric antibodies such as humanized murine antibodies.

Other suitable techniques involve selection of libraries of recombinant antibodies in phage or similar vectors (see, e.g., Huse, et al., *Science* 246:1275–1281 (1989); Ward, et al., *Nature* 341:544–546 (1989); and Vaughan, et al., *Nature Biotech.* 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild, et al., *Nature Biotech.* 14:845–851 (1996).

Frequently, the CD97 proteins and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al., *Proc. Nat'l Acad. Sci. USA* 86:10029–10033 (1989).

The antibodies of this invention are also used for affinity chromatography in isolating CD97 protein. Columns are prepared, e.g., with the antibodies linked to a solid support, e.g., particles, such as agarose, SEPHADEX®, or the like, where a cell lysate is passed through the column, washed, and treated with increasing concentrations of a mild denaturant, whereby purified CD97 protein are released.

In one aspect of the invention, the antibodies are used to screen expression libraries for particular expression products such as normal or abnormal human CD97 protein, or used to screen T-cell expression libraries from other mammalian species. Usually the antibodies in such a procedure are labeled with a moiety allowing easy detection of presence of antigen by antibody binding.

In a further aspect of the invention, antibodies raised against a CD97 protein are also used to raise anti-idiotypic antibodies. These are useful for detecting or diagnosing various pathological conditions related to the presence of the respective antigens.

B. Human or Humanized (Chimeric) Antibody Production

In one embodiment of the invention, the anti-CD97 protein antibodies of this invention are administered to a mammal (e.g., a human patient) for therapeutic purposes (e.g., as targeting molecules when conjugated or fused to effector molecules such as labels, cytotoxins, enzymes, growth factors, drugs, etc.). Antibodies administered to an organism other than the species in which they are raised are often immunogenic. Thus, for example, murine antibodies administered to a human often induce an immunologic response against the antibody (e.g., the human anti-mouse antibody (HAMA) response) on multiple administrations. The immunogenic properties of the antibody are reduced by altering portions, or all, of the antibody into characteristically human sequences thereby producing chimeric or human antibodies, respectively.

1. Humanized (Chimeric) Antibodies

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g. U.S. Pat. Nos: 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). Detailed methods for preparation of chimeric (humanized) antibodies can be found in U.S. Pat. No. 5,482,856.

2. Human Antibodies

In another embodiment, this invention provides for fully human anti-CD97 protein antibodies. Human antibodies consist entirely of characteristically human polypeptide sequences. The human anti-CD97 protein antibodies of this invention can be produced in using a wide variety of methods (see, e.g., Boyle, et al., U.S. Pat. No. 5,654,407 and Larrick, et al., U.S. Pat. No. 5,001,065 for review).

In preferred embodiments, the human anti-CD97 protein antibodies of the present invention are produced initially in trioma cells. Genes encoding the antibodies are then cloned and expressed in other cells, particularly, nonhuman mammalian cells. The general approach for producing human antibodies by trioma technology has been described by Ostberg, et al., *Hybridoma* 2:361–367 (1983), Ostberg, U.S. Pat. No. 4,634,664, and Engelman, et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

The genes encoding the heavy and light chains of immunoglobulins secreted by trioma cell lines are cloned according to methods known to those of skill in the art, including the polymerase chain reaction (see, e.g., Sambrook et al.; Berger & Kimmel; and Co, et al., *J. Immunol.* 148:1149 (1992). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

V. CD97 Protein Immunoassays

Means of detecting the CD97 proteins of the present invention are not critical aspects of the present invention. In a preferred embodiment, the CD97 proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology Volume 37: Antibodies in Cell Biology, Asai, ed. Academic Press, Inc. New York (1993); Basic and Clinical Immunology, 7th Ed., Stites & Terr, eds. (1991). Immunological binding assays (or immunoassays) typically utilize a "capture agent" to specifically bind to and often immobilize the analyte (in this case CD97 protein). The capture agent is a moiety that specifically binds to the analyte. In a preferred embodiment, the capture agent is an antibody that specifically binds a CD97 protein(s). The antibody (anti-CD97 protein antibody) may be produced by any of a number of means known to those of skill in the art as described herein.

Immunoassays often utilize a labeling agent to specifically bind to and label the binding complex formed by the capture agent and the analyte. The labeling agent may itself be one of the moieties comprising the antibody/analyte complex. Thus, the labeling agent may be a labeled CD97 protein or a labeled anti-CD97 protein antibody. Alternatively, the labeling agent may be a third moiety, such as another antibody, that specifically binds to the antibody/CD97 protein complex.

In some embodiments, the labeling agent is a second CD97 protein antibody bearing a label. Alternatively, the second CD97 protein antibody lacks a label, but it is, in turn, bound by a labeled third antibody specific to antibodies of the species from which the second antibody is derived. The second may be modified with a detectable moiety, such as biotin, to which a third labeled molecule can specifically bind, such as enzyme-labeled streptavidin.

In another aspect of immunoassays, other proteins capable of specifically binding immunoglobulin constant regions, such as protein A or protein G are used as the label agent. These proteins are normal constituents of the cell walls of streptococcal bacteria. They exhibit a strong non-immunogenic reactivity with immunoglobulin constant regions from a variety of species (see, generally Kronval, et al., *J. Immunol.* 111:1401–1406 (1973), and Akerstrom, et al., *J. Immunol.* 135:2589–2542 (1985)).

Throughout the assays, incubation and/or washing steps are typically required after each combination of reagents. Incubation steps vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a CD97 protein in a biological sample generally comprises the steps of contacting the biological sample with an antibody which specifically reacts, under immunologically reactive conditions, to the CD97 protein. The antibody is allowed to bind to the CD97 protein under immunologically reactive conditions, and the presence of the bound antibody is detected directly or indirectly.

A. Non-Competitive Assay Formats

Immunoassays for detecting CD97 proteins of the present invention include competitive and noncompetitive formats. Noncompetitive immunoassays are assays in which the amount of captured analyte (in this case CD97 protein) is directly measured. In one preferred "sandwich" assay, for example, the capture agent (anti-CD97 protein antibodies) can be bound directly to a solid substrate where they are immobilized. These immobilized antibodies then capture CD97 protein present in the test sample. The CD97 protein thus immobilized is then bound by a labeling agent, such as a second human CD97 protein antibody bearing a label. Alternatively, the second CD97 protein antibody lacks a label, but is, in turn, bound by a labeled third antibody specific to antibodies of the species from which the second antibody is derived. The second antibody may be modified with a detectable moiety, such as biotin, to which a third labeled molecule can specifically bind, such as enzyme-labeled streptavidin.

B. Competitive Assay Formats

In competitive assays, the amount of analyte (CD97 protein) present in the sample is measured indirectly by measuring the amount of an added (exogenous) analyte (CD97 protein) displaced (or competed away) from a capture agent (anti CD97 protein antibody) by the analyte present in the sample. In one competitive assay, a known amount of CD97 protein is added to the sample and the sample is then contacted with a capture agent, e.g., an antibody that specifically binds CD97 protein. The amount of CD97 protein bound to the antibody is inversely proportional to the concentration of CD97 protein present in the sample.

In some embodiments, the antibody is immobilized on a solid substrate. The amount of CD97 protein bound to the antibody is determined either by measuring the amount of CD97 protein present in a CD97 protein/antibody complex, or by measuring the amount of remaining uncomplexed CD97 protein. The amount of CD97 protein may be detected by providing a labeled CD97 protein molecule.

A hapten inhibition assay is another preferred competitive assay. In this assay a known analyte, in this case CD97 protein is immobilized on a solid substrate. A known amount of anti-CD97 protein antibody is added to the sample, and the sample is then contacted with the immobilized CD97 protein. In this assay, the amount of anti-CD97 protein antibody bound to the immobilized CD97 protein is inversely proportional to the amount of CD97 protein present in the sample. Again the amount of immobilized antibody is detected by measuring either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can be used for crossreactivity determinations. For example, one of the CD97α subunits is immobilized to a solid support. Proteins are added to the assay which compete with the binding of the antisera to the immobilized antigen. The ability of the proteins to compete with the binding of the antisera to the immobilized protein is compared to the binding by the CD97α subunit. The percent crossreactivity for the above proteins is calculated, using standard calculations. Those antisera with less than 10% crossreactivity with each of the proteins listed above are selected and pooled. The cross-reacting antibodies are optionally removed from the pooled antisera by immunoabsorption with the above-listed proteins.

The immunoabsorbed and pooled antisera are then used in a competitive binding immunoassay as described above to compare a second protein, thought to be perhaps the protein of this invention, to the immunogen protein (i.e. soluble CD97 subunit or an analog partially encoded by a partial nucleic acid sequence). In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded that is required, then the second protein is said to specifically bind to an antibody generated to an immunogen consisting of the partially encoded protein.

C. Other Assay Formats

In a particularly preferred embodiment, Western blot (immunoblot) analysis is used to detect and quantify the presence of soluble CD97 subunits or their analogs in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind soluble CD97 subunits or their analogs. Antibodies directed against soluble CD97 subunits or their analogs specifically bind to soluble CD97 subunits on the solid support. These antibodies may be directly labeled or alternatively may be subsequently detected using labeled antibodies (e.g., labeled sheep anti-mouse antibodies) that specifically bind to the soluble CD97 subunit antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34–41 (1986)).

1. Reduction of Non-Specific Binding.

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used with powdered milk being most preferred.

2. Labels.

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or 32P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

3. Substrates.

As mentioned above, depending upon the assay, various components, including the antigen, target antibody, or anti-human antibody, may be bound to a solid surface. Many methods for immobilizing biomolecules to a variety of solid surfaces are known in the art. For instance, the solid surface may be a membrane (e.g., nitrocellulose), a microtiter plate (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through non-specific bonding.

A wide variety of organic and inorganic polymers, both natural and synthetic may be employed as the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, Immobilized Enzymes, Ichiro Chibata, Halsted Press, New York, (1978), and Cuatrecasas, *J. Biol. Chem.* 245:3059 (1970)).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

VI. Diagnostic Methods

Those of skill will recognize that the diagnostic methods of the present invention are performed using any number of well known nucleic acid based assays. Nucleic acids selectively reactive, under stringent conditions, to a CD97 nucleic acid are provided for supra and may be employed in nucleic acid assays to detect, qualitatively and/or quantitatively, the level of CD97 expressed. However, the preferred diagnostic method is an immunoassay. An antibody composition of the diagnostic methods of the present invention includes at least one unique antibody, preferably at least two, and more preferably at least three unique antibodies. The antibodies are specifically reactive, under immunologically reactive conditions, to a mammalian CD97 α subunit. Preferably, the antibody composition is specifically reactive to each of the human CD97 subunits α1, α2, and α3. Antibodies to CD97 α subunits are discussed more fully supra. Those of ordinary skill will understand that specific reactivity can be achieved by processing of the biological sample prior to contact with the antibody composition so as to remove substantially cross-reactive compounds. Alternatively, specific reactivity is achieved by employing antibodies which are substantially specific to the CD97 α subunits such that binding to these antigens occurs to a detectably greater degree and/or to the substantial exclusion of binding to other antigens in the sample.

VII. Method of Detecting Inflammation

The present invention provides a method for determining the degree of inflammation at a site in a mammal. Inflammation typically occurs due to the presence of a localized antigen at the specified site. Leukocyte migration to the site of antigen localization occurs as part of the inflammatory cascade. Other phases of the inflammatory response include: specific and nonspecific recognition of foreign antigens mediated by T and B lymphocytes, macrophages, and the alternative complement pathway; amplification of the inflammatory response with recruitment of specific and nonspecific effector cells; and, macrophage, neutrophil, and lymphocyte participation in antigen destruction.

The method comprises the steps of contacting an antibody composition to a biological sample from the site at which the degree of inflammation is being determined. The biological sample may be a tissue sample from the site of inflammation. Most conveniently, the tissue sample is a fluid sample. The fluid may be lymph fluid, amniotic fluid, cerebrospinal fluid, blood, synovial fluid, sputum, urine, tears, or other cellular secretions or discharge from the site.

The antibodies are incubated under immunologically reactive conditions for sufficient time to permit a CD97 α subunit to bind to an anti-CD97 α antibody in the antibody composition to form an antibody:CD97 α subunit complex. Detection of the complex indicates the presence and amount of the CD97 α subunit in the sample.

Methods of performing immunoassays are well known in the art including, for example, ELISA, competitive immunoassays, radioimmunoassays, Western blots, indirect immunofluorescent assays and the like. See Harlow & Lane for a description of immunoassay formats and conditions.

VIII. Assays for CD97 Antagonists

A. CD97 Antagonists

1. Antisense

The effectiveness of antisense molecules in blocking target gene functions has been demonstrated in a number of different systems (Friedman et al., *Nature* 335:452–54 (1988), Malim et al., *Cell* 58:205–14 (1989) and Trono et al., *Cell* 59:113–20 (1989)). In general, a vector which includes a DNA segment encoding a soluble CD97 subunit antisense transcript, which is complementary to a segment of the soluble CD97 subunit gene, is introduced into and expressed in a target cell that expresses the soluble CD97 subunit gene. The expressed antisense strand interacts with the sense stand and prevents proper processing of the sense stand.

Ribozymes may also be used to target the mRNA encoding the soluble CD97 subunit protein.

2. Synthetic Molecules

Synthetic drugs targeted to specific proteins generally act by interacting with and inhibiting the activity of the target protein. The soluble CD97 subunit assays provided herein are useful to identify inhibitors of those activities. To do so, the activity of soluble CD97 subunits are assayed in the presence and absence of a test substance, such as a synthetic or isolated naturally occurring chemical inhibitor (in particular peptides or other ligands that bind to the active site or to allosteric sites of the soluble CD97 subunit). An inhibitor of soluble CD97 subunit depresses the activity of soluble CD97 subunit at least 50%, preferably at least 90%, and most preferably at least 99%.

3. Antibodies

Antibodies can be used to bind to membrane-bound CD97 as well as shed proteins such as soluble CD97 subunit. The antibodies can be used to block binding of a protein to membrane-bound CD97 as well as block the binding of soluble CD97α subunits to cell surface receptors.

B. Screening for CD97 Antagonists

The present invention encompasses developing antisense protocols and antagonists that specifically inhibit the soluble CD97 subunit or the expression of the soluble CD97 subunit of the invention. The detection and testing of such inhibitors is made possible by the ability to make and obtain the claimed soluble CD97 subunit using methods described herein.

In one embodiment, assays for identification of a CD97 antagonist involves detecting the presence, absence, or quantity (e.g., genomic DNA copy number, or amount of transcript) of the CD97 gene or gene product in the presence of suspected antagonists. Gene products include nucleic acids derived from the gene or polypeptides encoded by the soluble CD97 subunit gene or nucleic acids derived therefrom.

C. Detection/Quantification of the Soluble CD97 Subunit Gene or Gene Product and Agents that Bind to the Gene or Gene Product The soluble CD97 subunit and/or its gene or gene product (i.e., mRNA) is preferably detected and/or quantified in a biological sample. As used herein, a biological sample is a sample of biological tissue or fluid that, in a healthy and/or pathological state, contains soluble CD97 subunit nucleic acid or the polypeptide. Such samples include, but are not limited to, sputum, blood, blood cells (e.g., white cells), tissue or fine needle biopsy samples, peritoneal fluid, pleural fluid, intraarticular fluid, cerebral spinal fluid, abscess exudate, or cells therefrom. Biological samples also include aortic walls and sections of tissues such as frozen sections taken for histological purposes. Although the sample is typically taken from a human patient, the assays can be used to detect soluble CD97 subunit genes or gene products in samples from any mammal, such as dogs, cats, sheep, cattle, and pigs.

The sample may be pretreated as necessary by dilution in an appropriate buffer solution or concentrated, if desired.

1. Nucleic Acid Assays.

In one embodiment, this invention provides for methods of detecting and/or quantifying soluble CD97 subunit expression by assaying the underlying soluble CD97 subunit gene (or a fragment thereof) or by assaying the soluble CD97 subunit gene transcript (mRNA). The assay is for the presence or absence of the normal gene or gene product, for the presence or absence of an abnormal gene or gene product, or quantification of the transcription levels of normal or abnormal soluble CD97 subunit gene product.

a. Nucleic Acid Sample

In a preferred embodiment, nucleic acid assays are performed with a sample of nucleic acid isolated from the patient to be tested. In the simplest embodiment, such a nucleic acid sample is the total mRNA isolated from a biological sample.

The nucleic acid (e.g., either genomic DNA or mRNA) is isolated from the sample according to any of a number of methods well known to those of skill in the art. One of skill will appreciate that where alterations in the copy number of the soluble CD97 subunit gene are to be detected, genomic DNA is preferably isolated. Conversely, where expression levels of a gene or genes are to be detected, preferably mRNA is isolated.

b. Hybridization Assays

A variety of methods for specific soluble CD97 subunit-related DNA and RNA measurements using nucleic acid hybridization techniques are known to those of skill in the art and described above (see also, Sambrook, supra).

c. Amplification Based Assays

In another embodiment, the soluble CD97 subunit gene or gene product can be detected (assayed) using an amplification based assay. In an amplification based assay, all or part of the soluble CD97 subunit gene or transcript (e.g., mRNA or cDNA) is amplified using primers described above and the amplification product is then detected. Amplification-based assays are well known to those of skill in the art and are described above (see, e.g., Innis, supra).

2. Detection of Expression Levels.

Where it is desired to quantify the transcription level (and thereby expression) of soluble CD97 subunit genes in a sample, the nucleic acid sample is one in which the concentration of the mRNA transcript(s) of the soluble CD97 subunit gene, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls are run to correct for variations introduced in sample preparation and hybridization as described herein. In addition, serial dilutions of "standard" target mRNAs are used to prepare calibration curves according to methods well known to those of skill in the art. Of course, where simple detection of the presence or absence of a transcript is desired, no elaborate control or calibration is required.

The expression of the soluble CD97 subunit gene is also detected and/or quantified by detecting or quantifying the expressed soluble CD97 subunit polypeptide. The soluble CD97 subunit polypeptides are detected and quantified by any of a number of means well known to those of skill in the art. These include analytical biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay(RIA), enzyme-linked immunosorbent assays (ELISAs), immunofluorescent assays, western blotting, as described above.

3. Scoring of the Assay.

The assays of this invention as scored (as positive or negative for soluble CD97 subunit) according to standard methods well known to those of skill in the art. The particular method of scoring will depend on the assay format and choice of label. For example, a western Blot assay is scored by visualizing the colored product produced by the enzymatic label. A clearly visible colored band or spot at the correct molecular weight is scored as a positive result, while the absence of a clearly visible spot or band is scored as a negative. In a preferred embodiment, a positive test will show a signal intensity (e.g., soluble CD97 subunit quantity) at least twice that of the background and/or control and more preferably at least 3 times or even at least 5 times greater than the background and/or negative control.

To one of skill in the art, it can be seen that the above assays can be used to screen for compositions that bind to the soluble CD97 subunit gene or one of its gene products. For example, if the suspected composition acts by binding to mRNA, amplification assays or northern transfers are used to quantify the amount of mRNA synthesized by the bacteria in the presence of the suspect composition.

D. Screening for Agents that Bind to Soluble CD97 Subunit Polypeptides

The assays described above for the detection of protein during the purification process can also be used to screen for agents that bind to soluble CD97 subunit. For example, synthetic compounds suspected of inhibiting CD97 binding are used in competitive immunoassays for soluble CD97 subunit. If the synthetic compound binds to soluble CD97 subunit such that the antibody binding site is not available to the antibody, the level of soluble CD97 subunit observed in the assay will be lower than the levels observed in broth from cells not grown in the presence of the suspect agent.

E. Bacterial Reporter Strains to Assay for Antagonists of the Soluble CD97 Subunit Gene 1. Bacterial Reporter Strains to Identify Expression of Soluble CD97 Subunits.

This section provides for a method of determining the expression and of quantifying soluble CD97 subunit in vivo and in vitro. This determination is premised on the discovery that it is possible to produce cells carrying recombinantly introduced reporter genes where the reporter gene product is expressed at sufficiently high levels so that it is detectable in the cells or homogenates of tissues or the tissues themselves. Reporter genes are genes that are operably linked to the nucleic acid sequence of interest and express an easily assayable product. Detection of the assayable product indicates the presence, absence or quantity of the reporter gene which, in turn, indicates the presence, absence, or quantity of soluble CD97 subunit. Reporter genes are well known to those of skill in the art. They include, but are not limited to genes expressing bacterial chloramphenicol acetyl transferase (CAT), beta-galactosidase (β-gal), various bacterial luciferase genes encoded by *Vibrio harveyi, Vibrio fischeri,* and *Xenorhabdus luminescens,* the firefly luciferase gene FFlux, and the like.

Cells carrying reporter genes are referred to herein as "reporter strains". As indicated above, reporter strains may be utilized to quantify the number of cells carrying the reporter gene in a particular sample. It will be appreciated by one of skill in the art that numerous types of cells are suitable for modification as reporter strains and the selection of a particular cell type depends on the particular protein to be expressed, in this case soluble CD97.

A reporter strain expressing high levels of a reporter gene product that is amenable to detection in a sensitive assay system allows the detection of relatively few cells. This high sensitivity makes it possible to detect differences in cell number after relatively short culture conditions thereby permitting assays having rapid throughput.

2. Assays Utilizing Bacterial Reporter Strains

In one aspect of the invention, assays are provided for in which the therapeutic or prophylactic composition is applied to a culture of cells expressing CD97 or its subunits.

(1) Culture Assays

The present invention provides for methods of screening CD97 antagonist activity in compositions using an in vitro, culture assay. In general, these assays comprise culturing reporter strains, exposing the cultured cells to a chemical composition, and then subsequently assaying for the reporter gene to determine differences in culture growth between the treated cells and untreated control cultures (see, for example, Cooksey et al. (1993) supra.).

Samples of the cultures are taken, and assayed for luminescence. The measure of luminescence is a function of the concentration of the reporter strain which, in turn, reflects the antigonist activity of the test composition. Comparison of the treated cultures with untreated cultures provides a measure of the efficacy of the antagonist.

a. Assaying Reporter Strains in Culture

The detection of reporter strains in culture has been previously described (see Cooksey et al., (1993) supra.

In one aspect, this invention provides a method of detecting chemiluminescent reporter strains where the method simply involves suspending the cells in a buffer, adding substrate and detecting the resulting illumination using a luminometer. Many suitable buffers are known to those of skill in the art. A preferred buffer is 100 mM $Na_3$-citrate at pH 5.1. Typically, the substrate is made up according to standard methods in the same buffer as the sample. In a preferred embodiment, the substrate will be made up as a 1 mM solution in a buffer, e.g. in 100 mM $Na_3$-citrate at pH 5.1. Many luminometers include a provision for autoinjecting the sample with substrate. In this case, the cells are inserted in the luminometer and read directly.

In a particularly preferred embodiment, the assay involves taking one or more 10 μL sample of the culture(s) and adding each sample to 90 μL of buffer (preferably 100 mM $Na_3$-citrate at pH 5.1) in a well of an opaque 96 well microtiter plate to produce one or more 100 μL test samples. The samples are preferably analyzed in a 96 well microtiter plate luminometer (e.g., EG&G Berthold model LB96P luminometer). The luminometer injects 100 μL of substrate made up as a 1 mM solution in 100 mM $Na_3$-citrate at pH 5.1. The luminometer is operated according to standard procedures (e.g. the model LB96P luminometer is run with a 15 second integration period and 0.5 second background sampling) provide a measure of luminescence.

The RLU reading is normalized to the number of cells resulting in a luminescence expressed as RLU/cell. Means of determining cell counts are well known to those of skill in the art.

b. Assaying Reporter Strains in Tissue Homogenates

Cells expressing the product of the reporter gene at high levels may be detected in simple tissue homogenates.

In general, in vivo detection of reporter strains involves obtaining a biological sample (e.g. a tissue or organ) from a transgenic animal containing the reporter strain. The biological sample contains the reporter strain as a consequence of the transgene and quantification of the reporter strain in the sample is a measure of the level of expression of the gene in the animal. The sample (tissue) is homogenized by any of a number of means known to those of skill in the art (e.g. a blender, a tissue grinder, etc.). The tissue is preferably homogenized in a buffer, for example phosphate buffered saline pH 7.4. The a buffer may additionally contain a non-ionic detergent (e.g., Triton X-100) which may lyse the host cells. The detergent also, decreases the viscosity and prevents congealing of the homogenate.

In a particularly preferred embodiment, the homogenate is adjusted to provide 5% wt/volume of tissue to buffer/detergent which is then diluted to 0.5% (wt/vol) in the assay buffer. The detergent is present at about 1%. Substrate is added to the sample solution and the resulting luminescence is quantified according to any of a number of methods well known to those of skill in the art, most preferably by the use of a luminometer.

In a preferred embodiment, the homogenate is assayed for luminescence in a 96 well microtiter plate format. For example, for an assay utilizing an EG&G Berthold model LB96P luminometer, a 10 $\mu$L aliquot of the homogenate is added to 90 $\mu$L of phosphate buffered saline (PBS) 7.4 containing 1% Triton X-100 to make a sample solution of 0.5% wt/volume to tissue to buffer/detergent. The assay is initiated when 100 $\mu$L of a 1 mM solution of substrate in a buffer (e.g. 100 mM $Na_3$-citrate at pH 5.1) is added to the sample solution. With the model LB96P, the readings are made with an integration period of 15 seconds, a background measurement time of 0.5 seconds and a background warning level of 500 RLU/sec.

F. Method of Identifying a Compound Inhibiting CD97 $\alpha$ Expression

The present invention also provides a method for identifying compounds which inhibit CD97 $\alpha$ subunit expression. The method comprises the steps of contacting the tested compound with a resting T-cell, in the presence of an effective amount of a T-cell mitogen. Contacting the compound may occur before, after, or simultaneous with contacting the resting T-cell with the effective amount of mitogen. T-cell mitogens are known in the art and include phytohemagglutinin (PHA), concanavalin A (ConA), phorbol 12-myristate 13-acetate (PMA), and pokeweed mitogen (PWM).

The T-cell is contacted with the compound under cell culture conditions supportive of T-cell activation. Culture conditions supportive of T-cell activation are known in the art and provided in the working examples disclosed herein. Generally, the compound will be present at a concentration of at least 1 nM, more typically at least 10 nM, preferably at least 100 nM, more preferably at least 1 $\mu$M, most preferably at least 10 $\mu$M, and frequently at a concentration of at least 100 $\mu$M.

An additional functional assay for a presumptive CD97 $\alpha$ subunit includes assaying for its effect on vascularization. In a preferred assay, an insoluble matrix, such as Matrigel, comprising the putative CD97 $\alpha$ subunit and fibroblast growth factor (basic or acidic) is injected into mice. Passaniti, et al., *Methods in Laboratory Investigation* 67:519–528 (1992), incorporated herein by reference. CD97 $\alpha$ can be identified by its effect in promoting vascularization relative to a control lacking the presumptive CD97 $\alpha$ subunit.

An additional functional assay comprises use of the presumptive CD97 $\alpha$ subunit in the presence of melanoma cells (e.g., A2058 cells, ATCC NO: CRL 11147) bearing the integrin $\alpha_v\beta_3$ receptor. See, Asnavoorian, et al., *J. Cell Biol.* 110:1427–1438 (1990). A localized concentration of CD97 $\alpha$ (e.g., 1 to 100 mg/mL, preferably 20 to 50 mg/mL) will cause the melanoma cells to migrate up the concentration gradient.

In yet another functional assay, the effects of a sample presumptively comprising soluble CD97 $\alpha$ subunit on bovine aortic endothelial cells (BAEC) or human aortic smooth muscle cells (HASM) is measured. CD97 $\alpha$ has been found to be an adhesion factor for both types of cells. Briefly, the sample presumptively containing the CD97 $\alpha$ subunit is coated onto wells of a 96 well plate. Cells are added to the plate and the plate is incubated at 37° C. long enough for the cells to adhere. After washing, the number of cells remaining are quantitated by methods well known in the art, including but not limited to, conversion of MTT, Crystal Violet staining, and fluorescent dyes (CELL-TITER 96®; Promega, Madison, Wis.).

Soluble CD97 $\alpha$ has also been found to be a chemotactic factor for HASM. Therefore in an assay analogous to that described above, the migration of HASM in a concentration gradient containing a sample is used to establish the presence of CD97 $\alpha$ in that sample.

In the present methods, the levels of CD97 $\alpha$ subunit are assayed. In preferred embodiments, the CD97 $\alpha$ subunit assayed for is selected from the group consisting of $\alpha1$, $\alpha2$, and $\alpha3$. An increased or decreased level of CD97 $\alpha$ subunit relative to a control lacking the compound (i.e., a negative control) indicates whether the compound increases or decreases CD97 $\alpha$ expression, respectively. Generally, a compound which increases or inhibits CD97 $\alpha$ expression yields a change in expression at least twice that of a control, often at least three times that of a control, preferably at least four times that of a control.

The method of assaying for changes of CD97 expression is not a critical aspect of the invention. The level of CD97 can be assayed by nucleic acid assays using nucleic acid probes to CD97 mRNA. CD97 $\alpha$ nucleic acids of the present invention as well as nucleic acid assays are discussed and referenced more fully, supra. In preferred embodiments, the level of CD97 is assayed using antibodies specifically reactive to a CD97 $\alpha$ subunit. Antibodies specifically reactive to CD97 $\alpha$ are described more fully, supra.

G. High-Throughput Screening Soluble CD97 Subunit Antagonists

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

1. Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. *J. Pept. Prot. Res.* 37:487–493 (1991), Houghton et al., *Nature* 354:84–88 (1991)). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with a β-D- glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho, et al., *Science* 261:1303 (1993)), and/or peptidyl phosphonates (Campbell et al., *J. Org. Chem.* 59:658 (1994)). See, generally, Gordon et al., *J. Med. Chem.* 37:1385 (1994), nucleic acid libraries, peptide nucleic acid libraries (see, e.g., U.S. Pat. No. 5,539,083) antibody libraries (see, e.g., Vaughn et al., *Nature Biotechnology* 14(3):309–314 (1996)), and PCT/US96/10287), carbohydrate libraries (see, e.g., Liang et al., *Science* 274:1520–1522 (1996), and U.S. Pat. No. 5,593,853), and small organic molecule libraries (see, e.g., benzodiazepines, Baum, C&EN, Jan. 18, 1993 p. 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

2. High Throughput Assays of Chemical Libraries

Any of the assays for CD97 antagonists described herein are amenable to high throughput screening. As described above, having identified the nucleic acid which encodes soluble CD97, likely drug candidates either inhibit expression of the gene product, or inhibit the activity of the expressed protein. Preferred assays thus detect inhibition of transcription (i.e., inhibition of mRNA production) by the test compound(s), inhibition of protein expression by the test compound(s), or binding to the gene (e.g., gDNA, or cDNA) or gene product (e.g., mRNA or expressed protein) by the test compound(s). Alternatively, the assay can detect inhibition of the characteristic activity of the gene product or inhibition of or binding to a receptor or other transduction molecule that interacts with the gene product.

High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configuarable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

IX. Method of Inhibiting Inflammation, Atherosclerosis and Angiogenesis The CD97 α subunits act in the establishment and maintenance of inflammation and atherosclerosis. The CD97 α subunits also act in the initiation of angiogenesis. Accordingly, the present invention provides methods for promoting and interfering in the induction and sustenance of inflammation. The present invention also provides methods for initiating or inhibiting angiogenesis, generally but not exclusively associated with chronic inflammation. Furthermore, the present invention provides methods for ameliorating atherosclerosis. Inhibiting the expression of CD97 α or β subunits, functionally inactivating CD97 α or β subunits (e.g., by binding to antibodies), or employing functionally inactive CD97 α subunit antagonists can be used to modulate endogenous CD97 function.

A. Inhibition of Angiogenesis

The preferred method for inhibiting angiogenesis comprises administering a therapeutically effective amount of a CD97 subunit antagonist, wherein the CD97 subunit is selected from the group consisting of α1, α2, α3, and β. The CD97 subunits are discussed more fully supra. The CD97 antagonist is selected from the group consisting of CD97 antisense nucleic acid, anti-CD97 antibody, and decoy CD97 α, wherein the decoy CD97 α has at least one amino acid substitution within the Arg-Gly-Asp (SEQ ID NO:7) motif. In preferred embodiments, glutamic acid is substituted for aspartic acid. Generally, angiogenesis is associated with chronic inflammation including such disorders as rheumatoid arthritis, systemic lupus erythematosus, vasculitides (e.g., temporal arteritis), sarcoidosis, regional enteritis, and tissue injury (e.g., fracture).

B. Inhibition of Inflammation

The present invention provides a method of inhibiting CD97 associated inflammation in a mammal. The method comprises administering a therapeutically effective amount of a CD97 subunit antagonist, wherein the CD97 subunit is selected from the group consisting of α1, α2, α3, and β. The CD97 subunits are discussed more fully supra. The CD97 antagonist is selected from the group consisting of CD97 antisense nucleic acid, anti-CD97 antibody, and decoy CD97 α, wherein the decoy CD97 αhas at least one amino acid substitution within the Arg-Gly-Asp motif (SEQ ID NO:7). In preferred embodiments, glutamic acid is substituted for aspartic acid.

C. Inhibition of Atherosclerosis

The present invention provides a method of inhibiting CD97 associated atherosclerosis in a mammal. The method comprises administering a therapeutically effective amount of a CD97 subunit antagonist, wherein the CD97 subunit is selected from the group consisting of α1, α2, α3, and β. The CD97 subunits are discussed more fully supra. The CD97 antagonist is selected from the group consisting of CD97 antisense nucleic acid, anti-CD97 antibody, and decoy CD97 α, wherein the decoy CD97 α has at least one amino acid substitution within the Arg-Gly-Asp motif (SEQ ID NO:7). In preferred embodiments, glutamic acid is substituted for aspartic acid.

D. Pharmaceutical Compositions and Method of Administration

The formulations containing therapeutically effective amounts of CD97 antagonists of the present invention are either sterile liquid solutions, liquid suspensions or lyophilized versions and optionally contain stabilizers or excipients. Lyophilized compositions are reconstituted with suitable diluents, e.g., water for injection, saline, 0.3% glycine and the like. The compositions further comprise pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, and the like. Actual methods for preparing administrable compositions will be known or apparent to those skilled in the art and are described in more detail in such publications as Remington's Pharmaceutical Science, 19th ed., Mack Publishing Company, Easton, Pa. (1995).

The compositions for administration will commonly comprise a solution of the CD97 antagonist of the present invention dissolved in a pharmaceutically acceptable carrier, preferably an aqueous carrier. A variety of aqueous carriers are used, e.g., buffered saline and the like. These solutions are sterile and generally free of undesirable matter. These compositions are sterilized by conventional, well known techniques.

As will be readily understood by the clinician of ordinary skill in the art, the dose will be dependent upon the properties of the particular CD97 antagonist employed, e.g., its activity and biological half-life, the concentration of CD97 antagonist in the formulation, the site and rate of dosage, the clinical tolerance of the patient involved, the disease afflicting the patient, the severity of the disease, and the like.

1. Delivery of CD97 Antagonists

Protein based CD97 antagonists include inactive CD97 α mutants (decoy proteins) which compete with, and thereby inhibit, native CD97 α. Likewise anti-CD97 antibodies can be used to interfere in CD97 function. Protein-based CD97 antagonists will be administered topically or parenterally in a therapeutically effective dose ranging from about 10.0 mg to 100 mg per cubic centimeter of affected area. CD97 antagonists which are nucleic acid based (i.e., antisense compounds) can be administered topically or parenterally in a therapeutically effective dose ranging from about 0.25 to 25 nanomoles. In preferred embodiments, the antisense compounds are administered subcutaneously using a micro-osmotic pump at a rate of from 0.25 to 25 nanomoles/hour, most preferably at 2.5 nanomoles/hour. The dose of CD97 antagonist will depend upon the size of the area affected, the severity of the disease, and the potency of the specific CD97 antagonist administered. The parenteral formulation of protein based CD97 antagonists can be administered as a continuous intravenous infusion or as an intravenous (i.v.), intramuscular (i.m.), or subcutaneous (s.c.) injection. Topical administered CD97 antagonists can be delivered as the free protein or as part of a controlled delivery system.

In one aspect of delivery, C-5 propyne derivitized oligonucleotides which are complementary to at least 7 nucleotides of mRNA are used in antisense applications. See, Wagner, et al., *Nature Biotech.* 14(7):840–844 (1996), incorporated herein by reference. While statistically a 7-mer is expected to be complementary to a number of different messages within a cell, only a small subset of target sites are accessible due to differences in secondary and tertiary structure. Computer algorithms for determining secondary structure are known in the art. See e.g., Jaeger, et al., *Science* 244:48–52 (1989). Likewise, candidate C-5 propyne derivatized nucleotides of at least 7 nucleotides in length which are complementary to a CD97 subunit are used as CD97 antagonists. These antagonists are initially be selected for accessibility to regions of CD97 mRNA using computer models of mRNA secondary structure. Underivatized oligonucleotides of at least 17 nucleotides in length are also used. Alternatively, antisense oligonucleotides are expressed in vivo by operably linking a CD97 nucleic acid sequence or subsequence in reverse orientation to a promoter. Transfection of nucleic acids is accomplished using standard gene transfer methods: physical (e.g., electroporation, direct gene transfer, and particle bombardment), chemical (e.g., proteinoids, microemulsions, and liposomes), and biological (e.g., virus-derived vectors, and receptor-mediated uptake).

For example, Curiel and co-workers have demonstrated that naked plasmid DNA bound electrostatically to poly-L-lysine or poly-L-lysine-transferrin which has been linked to defective adenovirus mutants can be delivered to cells with transfection efficiencies approaching 90%. The adenovirus-poly-L-lysine-DNA conjugate binds to the normal adenovirus receptor and is subsequently internalized by receptor-mediated endocytosis. This approach has been used to obtain as much as a 1000-fold increase in expression of gene therapy vectors. Herpes viruses have similar properties. Curiel, et al., *Proc. Nat'l Acad. Sci. USA* 88:8850–8854 (1991); Cotten, et al., *Proc. Nat'l Acad. Sci. USA* 89:6094–6098 (1992); Curiel, et al., *Hum. Gene Ther.* 3:147–154 (1992); Wagner, et al., *Proc. Nat'l Acad. Sci.*

USA 89:6099–6103 (1992); Michael, et al., *J. Biol. Chem.* 268:6866–6869 (1993); Curiel, et al., *Am. J. Respir. Cell Mol. Biol.* 6:247–252 (1992); Harris, et al., *Am. J. Respir. Cell Mol. Biol.* 9:441447 (1993)); Gao, et al., *Hum. Gene Ther.* 4:17–24 (1993); and U.S. Pat. Nos. 5,547,932; 5,521,291.

In a further aspect of delivery, controlled release parenteral formulations of the CD97 antagonists of the present invention are made as implants, oily injections, or as particulate systems. For a broad overview of protein delivery systems see, Banga, Therapeutic Peptides and Proteins: Formulation, Processing, and Delivery Systems, Technomic Publishing Company, Inc. Lancaster, Pa. (1995), incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 tm are generally referred to as nanoparticles, nanospheres, and nanocapsules, respectively. Capillaries used to deliver nanoparticles intravenously have a diameter of approximately 5 $\mu$m. Microparticles are typically around 100 $\mu$m in diameter and are administered subcutaneously or intramuscularly. See, e.g., Kreuter, "Nanoparticles," in Colloidal Drug Delivery Systems, Kreuter, ed., Marcel Dekker, Inc., New York, N.Y., pp. 219–342 (1994); Tics & Tabibi, "Parenteral Drug Delivery: Injectibles," in Treatise on Controlled Drug Delivery, Kydonieus, ed., Marcel Dekker, Inc. New York, N.Y., pp.315–339 (1992), both of which are incorporated herein by reference. Numerous systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Polymers for use as controlled CD97 antagonists are generally biocompatible. Various degradable and nondegradable polymeric matrices for use in controlled drug delivery are known in the art. Langer, *Accounts Chem. Res.* 26:537–542 (1993). For example, the block copolymer, polaxamer 407 exists as a mobile viscous at low temperatures but forms a semisolid gel at body temperature. It has shown to be an efficacious vehicle for formulation and sustained delivery of recombinant interleukin-2 and urease. Johnston, et al., *Pharm. Res.* 9:425–434 (1992), Pec, et al., *J. Parent. Sci. Tech.* 44(2):58–65 (1990). Hydroxyapatite can also be used as a microcarrier for controlled release of proteins. Ijntema, et al., *Int. J. Pharm.* 112:215–224 (1994). Liposomes can be used for controlled release as well as drug targeting of entrapped drug. Betageri, et al., "Targeting of Liposomes," in Liposome Drug Delivery Systems, Technomic Publishing Co., Inc., Lancaster, Pa. (1993). See also, U.S. Pat. Nos. 4,235,871, 4,501,728, 4,837,028 4,957,735 and 5,019,369, each of which is incorporated herein by reference.

Preferably, the dosage is administered once but may be applied periodically until either a therapeutic result is achieved or until side effects warrant discontinuation of therapy. Generally, the dose should be sufficient to treat or ameliorate symptoms or signs of disease without producing unacceptable toxicity to the patient. An effective amount of the compound is that which provides either subjective relief of a symptom(s) or an objectively identifiable improvement as noted by the clinician or other qualified observer.

Solutions comprising CD97 antagonists of the present invention will typically have a pH in the range of pH 5 to 9.5. The buffer salts of the CD97 antagonist solution are typically phosphate, tris (hydroxymethyl) aminomethane-HCl, saline, or citrate and the like. Buffer concentrations are typically in the range of 1 to 100 mM. The CD97 antagonist solution further comprises a salt, such as sodium chloride or potassium chloride in a concentration of 50 to 150 mM. An effective amount of a stabilizing agent such as an albumin, a globulin, a gelatin, a protamine or a salt of protamine may also be included to a solution comprising the CD97 antagonist of the present invention.

X. Cellular Transfection and Gene Therapy

The present invention provides packageable CD97 subunit nucleic acids (cDNAs), supra, for the transfection of cells in vitro and in vivo. These packageable nucleic acids are inserted into any of a number of well known vectors for the transfection of target cells and organisms as described below. The nucleic acids are transfected into cells, ex vivo or in vivo, through the interaction of the vector and the target cell. The CD97 subunit nucleic acids are operably linked in reverse orientation to a promoter then expresses the CD97 antisense mRNA thereby mitigating the effects of CD97 overexpression. The CD97 subunit nucleic acids are any one of the integers from 17 to 25 nucleotides in length. Nucleic acids of the present invention are discussed more fully, supra. For a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Dillon, *TIBTECH* 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(l):31–44 (1995); Haddada, et al., Current Topics in Microbiology and Immunology, Doerfler & Böhm (eds), Springer-Verlag, Heidelberg Germany (1995); and Yu, et al., *Gene Therapy* 1:13–26 (1994).

Delivery of the gene or genetic material into the cell is the first step in gene therapy. A large number of delivery methods are well known to those of skill in the art. Such methods include, for example, liposome-based gene delivery (Debs & Zhu, WO 93/24640 (1993); Mannino & Gould-Fogerite, *BioTechniques* 6(7):682–691 (1988); Rose, U.S. Pat. No. 5,279,833; Brigham, WO 91/06309 (1991); and Felgner, et al., *Proc. Nat'l Acad. Sci. USA* 84:7413–7414 (1987)), and replication-defective retroviral vectors harboring a therapeutic polynucleotide sequence as part of the retroviral genome (see, e.g., Miller, et al., *Mol. Cell Biol.* 10:4239 (1990); Kolberg, *J. NIH Res.* 4:43 (1992), and Cometta, et al., *Hum. Gene Ther.* 2:215 (1991)). Widely used retroviral vectors include those based upon murine leukemia virus (MuLV), gibbon ape leukemia virus (GaLV), simian immuno deficiency virus (SIV), human immuno deficiency virus (HIV), and combinations thereof. See, e.g., Buchscher, et al., *J. Virol.* 66(5):2731–2739 (1992); Johann, et al., *J. Virol.* 66(5):1635–1640 (1992); Sommerfelt, et al., *Virol.* 176:58–59 (1990); Wilson, et al., *J. Virol.* 63:2374–2378 (1989); Miller, et al., *J. Virol.* 65:2220–2224 (1991); Wong-Staal, et al., PCT/US94/05700, and Rosenburg & Fauci, Fundamental Immunology, Third Edition, Paul (ed), Raven Press, Ltd., New York (1993), and the references therein, and Yu, et al., supra).

Avian adenovirus (AAV) based vectors are also used to transduce cells with target nucleic acids, e.g., in the in vitro production of nucleic acids and peptides, and in vivo and ex vivo gene therapy procedures. See, West, et al., *Virology* 160:38–47 (1987); Carter, et al., U.S. Pat. No. 4,797,368 (1989); Carter, et al., WO 93/24641 (1993); Kotin, *Hum. Gene Ther.* 5:793–801 (1994); Muzyczka, *J. Clin. Invest.*

94:1351 (1994) and Samulski (supra) for an overview of AAV vectors. Construction of recombinant AAV vectors are described in a number of publications, including Lebkowski, U.S. Pat. No. 5,173,414; Tratschin, et al., *Mol. Cell. Biol.* 5(11):3251–3260 (1985); Tratschin, et al., *Mol. Cell. Biol.* 4:2072–2081 (1984); Hermonat & Muzyczka, *Proc. Nat'l Acad. Sci. USA* 81:6466–6470 (1984); Samulski, et al., *J. Virol.* 63:03822–3828 (1989); and McLaughlin, et al., (1988). Cell lines that can be transfected by recombinant AAV include those described in Lebkowski, et al., *Mol. Cell. Biol.* 8:3988–3996 (1988).

A. Ex vivo Transfection of Cells

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with an CD97 antisense nucleic acid (gene or cDNA), and re-infused back into the subject organism (e.g., patient). Various cell types suitable for ex vivo transfection are well known to those of skill in the art (see, e.g., Freshney, et al., Culture of Animal Cells, a Manual of Basic Technique, 3rd Ed., Wiley-Liss, New York (1994)) and the references cited therein for a discussion of how to isolate and culture cells from patients).

As indicated above, in a preferred embodiment, the packageable nucleic acid which encodes a CD97 antisense is under the control of an activated or constitutive promoter. The transfected cell(s) express functional CD97 antisense nucleic acid which mitigates the effects resulting from overexpression of CD97.

In one particularly preferred embodiment, stem cells are used in ex-vivo procedures for cell transfection and gene therapy. The advantage to using stem cells is that they can be induced to differentiate into other cell types in vitro, or can be introduced into a mammal (such as the donor of the cells) where they will engraft in the bone marrow. Methods for differentiating $CD34^+$ cells in vitro into clinically important immune cell types using cytokines such a GM-CSF, IFN-$\gamma$ and TNF-$\alpha$ are known (see, Inaba, et al., *J. Exp. Med.* 176:1693–1702 (1992).

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as $CD4^+$ and $CD8^+$ (T cells), $CD45^+$ (panB cells), GR-1 (granulocytes), and $Ia^d$ (differentiated antigen presenting cells). For an example of this protocol see, Inaba, et al., *J. Exp. Med.* 176:1693–1702 (1992). In humans, bone marrow aspirations are typically from the posterior iliac bones and crests.

Alternatively, hematopoietic stem cells are isolated from fetal cord blood. Yu, et al., *Proc. Nat'l Acad. Sci. USA* 92:699–703 (1995) describe a preferred method of transducing $CD34^+$ cells from human fetal cord blood using retroviral vectors.

B. In vivo Transfection

In addition to ex vivo techniques, vectors (e.g., retroviruses, adenoviruses, liposomes, etc.) containing therapeutic nucleic acids are administered directly to the organism for transduction of cells in vivo. Administration is by any of the routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route will often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration comprise of liquid solutions, such as an effective amount of the packaged nucleic acid suspended in diluents, such as water, saline or PEG 400; capsules, sachets or tablets, each containing a predetermined amount of the active ingredient, as liquids, solids, granules or gelatin; suspensions in an appropriate liquid; and suitable emulsions. Tablet forms include one or more of the following: lactose; sucrose; mannitol; sorbitol calcium phosphates; corn starch; potato starch; tragacanth; microcrystalline cellulose; acacia; gelatin; colloidal silicon dioxide; croscarmellose sodium; talc; magnesium stearate; stearic acid; and other excipients; colorants; fillers; binders; diluents; buffering agents; moistening agents; preservatives; flavoring agents; dyes; disintegrating agents; and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

In another embodiment, packaged nucleic acids, alone or in combination with other suitable components, are made into aerosol formulations (i.e., nebulized) to be administered via inhalation. Preferably, aerosol formulations are placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, for example, by intraarticular, intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are administered, for example, by intravenous infusion, orally, topically, intraperitoneally, intravesically or intrathecally. Parenteral administration and intravenous administration are the preferred methods of administration. The formulations of packaged nucleic acid optionally are presented in unit-dose or multi-dose sealed containers, such as ampules and vials.

In yet another embodiment, injection solutions and suspensions are prepared from sterile powders, granules, and tablets of the kind previously described. Cells transduced by the packaged nucleic acid as described above in the context of ex vivo therapy are also administered intravenously or parenterally as described above.

The dose administered to a patient, in the context of the present invention will be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of CD97 antisense, the physician will evaluate circulating plasma levels of the vector, vector toxicities, progression of the disease, and the production of anti-vector antibodies. In general, the dose equivalent of a naked nucleic acid from a vector is from about 1 μg to 100 μg for a typical 70 kilogram patient, and doses of vectors which include a retroviral particle are calculated to yield an equivalent amount of therapeutic nucleic acid.

For administration, inhibitors and transduced cells of the present invention are administered at a rate determined by the LD-50 of the inhibitor, vector, or transduced cell type, and the side-effects of the inhibitor, vector or cell type at various concentrations, as applied to the mass and overall health of the patient. Administration is accomplished via single or divided doses.

In a preferred embodiment, prior to infusion, blood samples are obtained and saved for analysis. Between $10^8$ and $10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. If necessary, leukopheresis, transduction and reinfusion are repeated every 2 to 3 months. After the first treatment, infusions are performed on an outpatient basis at the discretion of the clinician. If the reinfusion is given as an outpatient, the participant is monitored for at least 4, and preferably 8 hours following the therapy.

Transduced cells are prepared for reinfusion according to established methods. See, Abrahamsen, et al., *J. Clin. Apheresis* 6:48–53 (1991); Carter, et al., *J. Clin. Apheresis*, 4:113–117 (1988); Aebersold, et al., *J. Immunol. Meth.* 112:1–7 (1988); Muul, et al., *J. Immunol. Meth.* 101:171–181 (1987); and Carter, et al., *Transfusion* 27:362–365 (1987). After a period of about 2–4 weeks in culture, the cells will number between $10^8$ and $10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

Although the present invention has been described in some detail by way of illustration and example for purposes of clarity of understanding, it will be obvious that certain changes and modifications may be practiced within the scope of the appended claims.

EXAMPLES

Example 1

Example 1 teaches the cloning of the intermediate isoformn (α2β) of CD97.

An 800 bp cDNA fragment (pAT 276) was cloned from a T-cell library enriched for mitogen-induced genes (Zipfel, et al., *Mol. Cell. Biol.* 9:1041–1048 (1989)). The induction of pAT276 mRNA following mitogen activation of T cells was verified by Northern blot analysis. pAT 276 was labeled with $^{32}P$ and used as a homologous probe to screen a randomly primed, cDNA library constructed from peripheral blood T-cells (PBT) that had been stimulated with PHA and PMA for 6 hours. Several overlapping clones were isolated, including one fall length 3.3 kb cDNA. Clones were subcloned into the BLUESCRIPT® vector (Stratagene) prior to sequencing. The nucleotide sequences were analyzed using the GCG package of programs (Genetics Computer Group, University of Wisconsin).

The predicted polypeptide sequence from full-length clone pAT276 was found to be 786 amino acids in length and contained a hydrophobic leader sequence in addition to seven stretches of hydrophobic residues in the carboxyl third of the protein. This is characteristic of membrane receptors that couple to heterotrimeric G proteins. In addition, a large extracellular domain of approximately 50 kD containing four EGF-like repeats and several potential Asn-linked glycosylation sites were also present.

The protein (SEQ ID NO:6) encoded by full-length clone pAT276 (SEQ ID NO:8) is shown in FIG. 1. FIG. 1 shows the structure of the three isoforms of CD97. Seven membrane spanning domains are underlined; the signal sequence is underlined and italicized; the RGD (SEQ ID NO:7) sequence is boxed; the EGF-like repeats are boxed and the repeats contained in the larger isoforms are shaded, potential N-linked glycosylation sites are within a diamond.

Full-length pAT276 demonstrated all the hallmarks of a 7TM (seven-pass transmembrane) protein including universally conserved cysteines in extracellular loops one and two and a cytoplasmic tail rich in serines and threonines and containing a putative palmitoylation site (O'Dowd, et al., *J. Biol. Chem.* 264:7564–7569 (1989); Ovchinnikov, et al., *FEBS Lett.* 230:1–5 (1988); Palczewski & Benovic, *Trends Biochem. Sci.* 16:387–391 (1991)). A database search for proteins related to pAT276 revealed that it is part of an evolutionarily conserved family of four proteins with large extracellular domains and uniquely related sequences defining a subfamily of 7TM proteins. The pAT276 protein is most closely related to EMR1 (Baud, et al., *Genomics* 26:334–344 (1995)), a widely-expressed protein of unknown function which is approximately 40% identical to the pAT276 protein in the amino terminal domain containing EGF-like repeats and approximately 45% identical in the carboxyl terminal 7TM region. Although both proteins are serine/threonine rich in the area between the EGF-like domain and the 7TM domain, they display only about 20% identity in that region. The 7TM domain of the pAT276 protein is also approximately 35% identical to the 7TM region of two predicted C. elegans proteins, B0286.2 and B0457.1, of unknown function that were identified as part of the genome sequencing effort in that organism. The predicted extracellular domains of B0286.2 and B0457.1 are unrelated to the pAT276 protein.

The 7TM regions encoded by pAT276, EMR1, B0286.2, and B0457.1 appear to define a subfamily most closely related to the glucagon receptor family of 7TM receptors. They display between 18–28% identity with members of the glucagon/secretin receptor family of 7TM receptors. A consensus for the glucagon family which is most evident in the transmembrane regions has been derived based upon conservation in at least 10/11 members of the glucagon family (Baud, et al., *Genomics* 26:334–344 (1995); Lok, et al., *Gene* 140:203–209 (1994)). pAT276 showed conservation of the glucagon family consensus only in the fourth transmembrane region, and EMR1, B0286.2, and B0457.1 similarly showed a pattern of imperfect conservation of the glucagon family consensus. There are several instances where protein pAT276, EMR1, B0286.2, and B0457.1 demonstrate identities among themselves that are not conserved with the glucagon receptor family members.

FIG. 2 shows a comparison of conserved motifs in CD97, EMR1, and fibrillin. The five EGF-like repeats encoded by fall-length pAT276 are related to the EGF-like repeats in EMR1 and to those in fibrillin. The first repeats of pAT276 and EMR1 are the most divergent relative to the other repeats within the proteins (Baud, et al., *Genomics* 26: 334–344 (1995)). Contained within the consensus sequence of EGF-like repeats for CD97, EMR1, and fibrillin is the Asp/Asn β-hydroxylation motif which is thought to enhance $Ca^{2+}$ binding (Selander-Sunnerhagen, et al., *J. Biol. Chem.* 267:19642–19649 (1992); Stenflo, et al., *Proc. Nat'l Acad. Sci. USA* 84: 368–372 (1987)). In CD97, approximately mid-way between the end of the EGF-like repeats and the start of the first membrane spanning sequence at position 318 is an Arg-Gly-Asp (RGD) (SEQ ID NO:7) motif, which is the binding site for several classes of integrins (Hynes, *Cell* 69:11–25 (1992)). A purified form of soluble CD97 α can serve as an integrin ligand.

Example 2

Example 2 describes the identification of three isoforms of CD97. RT-PCR analyses. Poly(A)+ RNA was isolated from purified human peripheral blood T cells activated with PHA and PMA. Two mg of poly(A)+ RNA was reverse transcribed to first-strand cDNA using random hexamer primers and SUPERSCRIPT II® RNase H reverse transcriptase (Gibco-BRL). One-twentieth of the reaction mixture was then subjected to specific PCR amplification as follows. PCR was performed for 1 cycle (94° C., 5 min), 30 cycles (94° C., 30 sec; 55–60° C., 1 min; 72° C., 2 min), and 1 cycle (72° C., 7 min), with PfuI DNA polymerase and one of three possible 5' primers: 276-38, 5'-GGCCGCGTCTTTCTCGCA-3' (SEQ ID NO:9); 276-20, 5'-AGATGTGGACGAATGTC-3' (SEQ ID NO:10); 276-6A, 5'-AAGACAAGCTCAGCCGA-3' (SEQ ID NO:11) and one of three possible 3' primers: 276-3, 5'-TGGGTTCATACAGCTGC-3' (SEQ ID NO:12); 276-6B, 5'-TCGGCTGAGCTTGTCTT-3' (SEQ ID NO:13); 276-15B, 5'-GCAGCTGTATGAACCCA-3' (SEQ ID NO:14). The PCR products were gel purified and sequenced directly using DTaq cycle sequencing kit (Amersham Life Science).

RT-PCR was performed utilizing activated T cell RNA and pAT276 derived primers to amplify and sequence alternative forms of pAT276-derived mRNAs. Three cDNA species were observed using primers which flanked the EGF-like repeat region. The middle form was identical to the pAT276 clone, while the upper form contained an additional EGF-like repeat which followed EGF-like repeat 3 of pAT276. The smallest form contained a total of three EGF-like repeats, having deleted pAT276 EGF-3.

Example 3

Example 3 teaches the identification and analysis of pAT276 (CD97) isoforms.
Antibody Production and Purification Polyclonal antibodies against conjugated peptides or bacterially expressed recombinant protein were raised in immunized rabbits. The peptides used for antibody production were anti-EGF3: CLPGFKFIPEDPKVC (SEQ ID NO:15) and anti-COOH: EFTSTTSGTGHNQTRA (SEQ ID NO:16). Oligopeptide antigens were prepared by glutaraldehyde conjugation to BSA. Anti-peptide antibodies were affinity purified using peptides conjugated to AFFI-GEL® supports (BioRad). A region of CD97 α2 encompassing residues 26 through 308 was subcloned into the histidine-tag bacterial expression vector pRSET® (Invitrogen) and recombinant protein was purified using a nickel-histidine purification method. CD97 specific antibodies were purified with an affinity column of recombinant antigen coupled to CNBr-activated SEPHAROSE® 4B (Pharmacia).
Cell Lines and Cell Cultures PBT were purified from leukophoreses by Ficoll gradient sedimentation followed by collection of nylon wool nonadherent cells (Irving, et al., (1989)). PBT were cultured in RPMI with 20 mM HEPES (pH 7.4) and 10% fetal calf serum (FCS) at a density of $2 \times 10^6$ cells/mL. T cells were stimulated with PHA-P (1 mg/mL; Burroughs Wellcome Co.) and PMA (20 ng/mL; Sigma). COS-7 cells were cultured in DMEM supplemented with 10% FCS, and they were transfected using the DEAE dextran method.
Metabolic Labeling PBT cells were incubated with equal amounts of $^{35}S$-methionine and $^{35}S$-cysteine in methionine and cysteine-free RPMI containing 10 mM HEPES and 5% dialyzed FCS. Steady-state labeling was carried out with 200 mCi of $^{35}S$/mL, $10^7$ cells/mL, and 2–4 hours of incubation. Pulse labeling was carried out with 1 mCi of $^{35}S$/mL, $10^8$ cells/mL, and 10 min of incubation followed by a 20-fold dilution with complete RPMI containing 10% FCS prior to collection at the indicated chase times.
Cell Lysis, Immunoprecipitation and Deglycosylation Cells were washed free of media and incubated for 15 min. on ice in lysis buffer: 50 mM Tris (pH 8.0), 150 mM NaCl, 5 mM EDTA, 10% glycerol, 1% NONIDET® P-40 (NP-40), and 1 COMPLETE™ protease inhibitor cocktail tablet/50 mL (Boehringer Mannheim). Cellular debris was pelleted at 110,000×g for 15 min. Material from 5 to $8 \times 10^6$ cells was immunoprecipitated with 10 μg of affinity purified antibody and 15 μL of protein A agarose (Gibco BRL) in a total volume of 1 mL for 2 to 16 hours with rotation at 4° C. Co-precipitation of CD97 β with antibodies directed against CD97 α was most apparent following short incubation times. The immune complexes were then washed three times; 20 min each with either lysis buffer or with lysis buffer containing 0.1% SDS. N-glycosidase F reactions were carried out directly after the immunoprecipitations by boiling samples in lysis buffer containing 0.5% SDS, followed by the addition of NP-40 to a final concentration of 2% and 10 units of recombinant N-glycosidase F and incubating the samples at 37° C. for 2 hours. Endoglycosidase H (Boehringer Mannheim) reactions were carried out by heating immunoprecipitation reactions in lysis buffer containing 0.1% SDS for 5 min at 100° C., followed by 5 fold dilution with lysis buffer and the addition of Endoglycosidase H (Boehringer Mannheim) to 10 units. Samples were incubated for 2 hours at 37° C.
Electrophoresis and Autoradiography Samples were electrophoresed through 7.5% or 10% SDS polyacrylamide gels using the Laemmli method (Sambrook, et al., (1989)). Dried gels were exposed to Kodak X-AR film or visualized on a Molecular Dynamics phosphorimager using IMAGEQUANT® software.
Immunoblot Analysis Electrophoretically separated proteins were transferred to nitrocellulose, and the filters were blocked (PBS, 10% horse serum, 0.1% TWEEN® 20) for at least 1 hour and subsequently incubated with the IgG fraction anti-$NH_2$ antibody at 5 μg/mL for 1 to 16 hours. The blot was washed in PBS+0.1% TWEEN® 20, incubated with goat anti-rabbit horseradish peroxidase (50 ng/mL) for 1 h at 37° C., and visualized by ECL.

Antibodies directed against recombinant pAT276 protein precipitated 3 proteins from activated T cells. However, Southern blot analyses demonstrated that pAT276 related sequences were encoded by a single gene. A sequence was published which matches the sequence of the smallest isoform (infra) of pAT276 containing 3 EGF-like repeats (Hamann, et al., (1995), supra). Therefore, the protein encoded by pAT276 is alternatively referred to as CD97.

Consistent with the nature of the three PCR-generated forms, transfection of pAT276 into COS cells and subsequent immunopreciptation of the encoded protein produced a protein band that co-migrated with the middle form of the proteins precipitated from activated T cells.

In order to characterize the biochemical properties of CD97, several antibodies were generated against different regions of the predicted sequence including the third EGF-like repeat of the middle and longest isoforms (anti-EGF3), residues 763–778 in the intracytoplasmic carboxyl tail (anti-COOH), and a recombinant peptide encompassing approximately the first half of the extracellular region (anti-$NH_2$). The comparison of proteins precipitated with antibodies directed against amino or carboxyl determinants revealed reactivity with distinct but associated peptides. Immunoprecipitation of metabolically labeled lysates from activated T cells with anti-$NH_2$ antibodies produced specifically precipitated proteins seen as a broad smear between about 75 and 90 kD and a protein of 28 kD. The 28 kD protein was observed in anti-$NH_2$ precipitations using certain nonstringent immunoprecipitation conditions. Removal of Asn-linked carbohydrate from anti- $NH_2$ immunoprecipitates showed 3 bands of approximately 45, 50, and 55 kD. The predicted molecular weights for the non-glycosylated forms of full-length CD97 are approximately 91, 84, and 79 kD, suggesting that the observed bands of 55, 50, and 45 kD represent proteolytically processed extracellular domains. This possibility was further suggested by the observation that antibodies directed to the COOH terminus of CD97 precipitated a 28 kD protein using denaturing conditions. Using nondenaturing conditions, anti-COOH antibodies precipitated the 28 kD protein in association with the CD97 isoforms recognized by amino-directed antibodies, suggesting a noncovalent association of the 28 kD protein with the three isoforms of the amino domain. Monoclonal antibodies A046 directed against CD97 (Pickl, et al., in Leukocyte Typing V: White Cell Differentiation Antigens, Schlossman, et al., (eds.), Oxford University Press, Oxford. pp. 1151–1153 (1995)) produced results similar to those seen with the anti-$NH_2$ antibodies. The two slower migrating forms of CD97 only were precipitated by anti-EGF3 antibodies as predicted from the cloning data showing that the smallest cDNA form was missing EGF-3.

Example 4

Example 4 describes pulse-chase analysis to verify that the CD97 amino isoforms and the 28 kD protein were processed from a common precursor.

Labeled lysates from activated T cells were immunoprecipitated with anti-EGF3 (which will recognize the intermediate and largest amino isoforms) or anti-COOH antibodies and were subsequently left untreated (A) or were deglycosylated with N-glycosidase F (B) or Endoglycosidase-H (C). See, Example 3. Stringent conditions were used for the immunoprecipitation reactions. The antibodies which recognize either amino or carboxyl localized determinants precipitate common pulse-labeled proteins of approximately 95 and 100 kD which disappear during the chase period inversely with the appearance of the expected processed products, and therefore, appear to represent nonproteolyzed precursors proteins. Deglycosylation of the 95 and 100 kD precursors was equivalent with either N-glycanase or Endoglycosidase H and revealed proteins of approximately 75, 80, and 85 kD, within the expected range for proteins encoded by the cloned cDNAs for CD97.

Immunoprecipitated protein from pulse-labeled COS-7 cells transfected with the pAT276 plasmid co-migrated with the 95 kD glycosylated or 80 kD deglycosylated precursor. In the lysates precipitated with anti-COOH antibodies, the 95 kD precursor was resolved as a doublet at lesser amounts of protein, representing the intermediate and smallest isoform precursors. The processed peptides were referred to as CD97 α1, α2, and α3 for the largest to smallest peptides, respectively, and CD97 β for the 28 kD peptide derived from the carboxyl end of the precursor.

The kinetics of CD97 precursor cleavage and the glycosylation pattern of the precursor and products have shown that the precursor is cleaved within 15 to 30 minutes after synthesis of the full-length peptide and prior to complex carbohydrate addition to the CD97 α isoforms. The precursor proteins were lost during the chase period with a half-life of about 15 minutes. The CD97 β did not appear to be glycosylated as its migration pattern was unaffected by treatment with endoglycosidases. For the two forms of CD97 α recognized by anti-EGF3 antibodies, precursor cleavage within the first 15 minute chase period produced peptides of 75 and 80 kD which were reduced to 50 and 55 kD following deglycosylation with either Endoglycosidase H or N-Endoglycosidase F. Therefore, the precursors are modified by high mannose-containing but not complex oligosaccharides. Between 15 and 30 minutes of chase, Endoglycosidase H-resistant (N-glycosidase F-sensitive) protein appeared which was observed as a smear between 75 and 95 kD and was concomitant with the loss of the substrates for complex carbohydrate addition observed as 75 and 80 kD peptides in untreated samples or as 50 and 55 kD peptides in Endoglycosidase H-treated samples. The mature CD97 α isoforms that had been modified by complex carbohydrate were observed readily after 60 minutes of chase.

Example 5

Example 5 describes analyses of the CD97 α isoforms and differential regulation of the α and β subunits.

Iodinations

Integral membrane proteins were labeled with $^{125}$I-iodonapthalene azide (INA), a cross-linking agent with high specificity for integral membrane proteins (Raviv, et al., *Biochemistry* 28:1313–1318 (1989)). PBT were washed in PBS and resuspended at $10^8$ cells/mL; 20 μL (10 μCi) of $^{125}$I-INA (Lofstrand Labs) was added to 200 μL of cells, vortexed, transferred to 2 $cm^2$ wells and irradiated with long-wave ultra-violet light for 2 min. Cross-linked cells were recovered and lysate from 20×$10^6$ cells was immunoprecipitated for each sample.

FACS analyses and labeling via surface iodination shows that the CD97 α isoforms are not large enough to extend into the membrane-spanning domains, yet they are clearly associated with the extracellular surface of the plasma membrane. Eichler, et al., *Scan. J. Immunol.* 39: 111–115 (1994); and Pickl, et al., supra. CD97 α's are not covalently associated with other proteins via disulfide bonds, but they are noncovalently associated with CD97 β. In order to determine whether such as association is necessary, we produced a truncated CD97 protein (CD97δ) that terminated just prior to the first membrane-spanning domain, and therefore, encoded a CD97 α-like molecule in the absence of CD97 β. DNA encoding full-length CD97 or CD97 δ was transfected into COS-7 cells which subsequently were analyzed for cell associated and secreted CD97 α protein. CD97 δ but not CD97 was secreted into the culture supernatants as determined by immunoprecipitation of metabolically labeled samples or western blotting, suggesting that the association of CD97 α and β is necessary to localize CD97 α to the extracellular membrane. Immunofluorescence analyses revealed intracellular but not membrane-associated fluorescence for CD97 δ. The size of the CD97 δ protein was approximately 5 kD larger than the normally processed CD97 α, suggesting that CD97 is normally processed approximately 45 amino acids $NH_2$-terminal to the first membrane spanning helix. The apparent lack of processing of the CD97 δ molecule despite the presence of the normal site of proteolysis further suggests that a linear sequence motif is not sufficient for recognition by a protease.

Steady state levels of CD97 α increased at least ten-fold in activated T-cells relative to resting T-cells. Because the anti-COOH antibodies did not recognize antigen in western blots, steady state levels of CD97 β were analyzed with a labeling technique. Cells were covalently labeled with $^{125}$I-INA and subsequently, the labeled cell lysates were immunoprecipitated with anti-COOH and anti-$NH_2$ antibodies. There was less than a two-fold difference in steady-state levels of CD97 β comparing resting versus activated T cells. As anticipated from its structure and extracellular localization, CD97 α was not labeled by $^{125}$INA. Thus, there appeared to be differential protein turnover for cell-associated CD97 α and β. The CD97 β observed in resting cells most likely resulted from stable protein synthesized during a prior stimulation and/or from a low level of constitutive CD97 mRNA.

Example 6

Example 6 describes the immunohistochemical analyses of CD97 α positive cells in a variety of inflammatory and some neoplastic conditions.

Patient Samples

Synovial fluid from knee joints were obtained from volunteers referred to the NIH Clinical Center for recent-onset arthritic pain or disability of less than 12 months duration and no previous diagnosis. In agreement with previously-published results for monoclonal antibodies defining CD97, it was found that the antibodies raised against CD97 α detected peripheral blood derived, activated T cells, activated B cells, granulocytes, and monocytes by FACS analyses. The cellular distribution of CD97 expression suggests a potential role in inflammatory processes.

Immunohistochemistry

Immunohistochemical studies were performed using fixed, paraffin-embedded sections and an avidin-biotin-peroxidase complex (ABC) method described previously (Hsu, et al., *J. Histochem. Cytochem.* 29:577–80 (1981)) using the Super Sensitive™ immunodetection system (BioGenex, San Ramon, Calif.) according to the manufacturers instructions. Antigen retrieval was performed on all samples by placing in 10 mM citrate buffer, pH 6.0, and heating for 40 min, under pressure, in a 700–1000 W microwave. The samples were left in the hot solution under pressure for an additional 30 min. Affinity purified anti recombinant anti-$NH_2$ antibody was used at 1 μg/mL. The following monoclonal antibodies were also assessed: A6 (CD45RO) (Zymed, San Francisco, Calif.), L26 (CD20) (DAKO, Carpenteria, Calif.), and Mb1 (HM57) (Kuzu, et al., *Histopathology* 22:141–144 (1993)).

Immunohistochemical analysis of samples from patients with chronic eczematous dermatitis demonstrated that high levels of CD97 α expression were observed on the majority of leukocytes which infiltrated inflammatory sites. There was superficial dermal, perivascular infiltration composed of predominantly T-lymphocytes (CD45RO$^+$), which exhibited a high level of CD97 α expression. High levels of CD97 α expression were also identified in the cutaneous infiltration of neoplastic T-lymphocytes in patients with mycosis fungoides (see Example 7) and in the macrophages of lymph node sinus histiocytosis. This contrasts with normal lymph nodes in which cells within follicles were predominantly negative and the cells in the intrafollicular region showed a gradient of CD97 α expression including a large percentage of unstained cells.

The differential turnover of CD97 α and CD97 β that was observed in resting and activated T cells coupled with the noncovalent association of CD97 α on the cell surface suggested that CD97 α may be shed into the interstitium. To address this possibility, we determined whether soluble CD97 α existed in cultured T cell supernatants (CS) or in body fluids including serum, synovial fluids (SF), or pleural effusions (PF). We detected CD97 α in cellular lysates (L) but not in the supernatants (CS) of activated T cells cultured for up to 96 hours. This was consistent with the results of COS-7 cells transfected with CD97. CD97 α was not found in normal serum or plasma. In contrast, CD97 α was found in several synovial fluids from individuals with inflammatory arthritis and in pleural fluid containing malignant B cell lymphoma and acute inflammatory cells. CD45, a highly-expressed integral membrane protein on leukocytes was assayed in parallel to CD97 α and found to be in cellular lysates but not in soluble form, suggesting that the observed CD97 a was not due to the presence of membrane fragments.

Example 7

Example 7 teaches a method of confirming mycosis fungoides or adult t-cell leukemia.

High levels of CD97 α expression are found in the cutaneous infiltration of neoplastic T-lymphocytes in patients with mycosis fungoides. Accordingly, the present invention also provides for a method of confirming the cutaneous T-cell lymphoma, mycosis fungoides (MF), in a biological sample obtained from a mammal (including humans). In the method, a biological sample is obtained from the patient. The biological sample is a biopsy of a skin lesion including papules, plaques, and tumors to ulcerations. T-lymphocytes in the sample are identified as CD3$^+$ and CD20$^-$ using antibodies available from commercial sources such as the American Type Culture Collection. The sample is incubated with an antibody composition selectively reactive, under immunologically reactive conditions, to a CD97 α subunit of the present invention. Detection of high levels of antibody:CD97 α subunit complex in the sample relative to its level in a normal control (i.e., not affected by a T-cell neoplasm or suffering from acute or chronic inflammation) is used to confirm the presence of MF in the patient.

The present invention further provides a means to confirm and distinguish adult T-cell leukemia (ATL) from mycosis fungoides. Both diseases present themselves with cutaneous infiltrations. However, while nearly 100% of neoplastic T-cells in patients with mycosis fungoides express high levels of CD97 α subunits, only about 20% to 30% of neoplastic T-cells from patients with ATL express high levels of CD97 α subunits relative to a normal control. Accordingly, the present invention aids in distinguishing between ATL and MF by assaying for a normal level of CD97 α subunit in a biological sample. The diagnosis is thus exclusive of MF.

The method comprises the steps of incubating a biological sample (preferably a skin biopsy) with an antibody composition which is selectively reactive, under immunologically reactive conditions, to a CD97 α subunit of the present invention. A normal level of CD97 α subunit, as measured relative to a control, excludes from the diagnosis MF. Conversely, a high level of CD97 α subunit in the sample aids in confirming the disease as MF. Methods of performing immunoassays are well known in the art and provided for, supra.

Example 8

Example 8 teaches the technique of removing bone marrow from human patients and isolating CD97-expressing hematopoeitic cells.

In humans, bone marrow aspirations from posterior iliac bones and crests are performed, e.g., under general anesthesia in the operating room. The bone marrow aspirations are approximately 1,000 mL in quantity. If the total number of cells collected is less than about $2\times10^8$/kg, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34. After the bone marrow is harvested, the mononuclear cells are separated from the other components by means of Ficoll gradient centrifugation. This is performed by a semi-automated method using a cell separator (e.g., a Baxter Fenwal CS3000+ or Terumo machine). The cells of lighter density, composed mostly of mononuclear cells are collected and the cells are incubated in plastic flasks at 37° C. for 1.5 hours. The adherent cells (monocytes, macrophages and B-cells) are discarded. The non-adherent cells are then collected and incubated with a monoclonal anti-CD34 antibody at 4° C. for 30 minutes with gentle rotation. The final concentration of the anti-CD34 antibody is 10 μg/mL. After two washes, paramagnetic microspheres (Dyna Beads, supplied by Baxter Inmmunotherapy Group, Santa Ana, Calif.) coated with sheep antimouse IgG (Fc) antibody are added to the cell suspension at a ratio of 2 cells/bead. After a further incubation period of 30 minutes at 4° C., the rosetted cells with magnetic beads are collected with a magnet. Chymopapain (Baxter Imunotherapy Group, Santa Ana, Calif.) at a final concentration of 200 U/mL is added to release the beads from the CD34+ cells. Alternatively, and preferably, an affinity column isolation procedure can be used which binds to CD34, or to antibodies bound to CD34. See, Ho, et al., *Stem Cells* 13(suppl. 3):100–105 (1995). See also, Brenner, *J. Hematother.* 2:7–17 (1993).

Example 9

Example 9 demonstrates the adhesion factor property of CD97 α for aortic endothelial cells and melanoma cells.

Adhesion was measured by the ability of bovine aortic endothelial cells and $\alpha_v\beta_3$ receptor-expressing A2058 melanoma cells to 96-well tissue culture plates. The wells were first coated with 10 μg of the extracellular domain of soluble CD97 α2 overnight. The cells were allowed to adhere for approximately three hours at 37° C. and washed extensively with phosphate buffered saline. The number of adherent cells were determined by TITER CELL 96® reagents (Promega; Madison, Wis.). The cells on the soluble CD97 α coated plates were spread out and flattened relative to cells adhering to wells coated with IgG (control).

In addition to adhesion factor properties, soluble CD97 α exhibits chemotaxis properties which also are indicative of the advancement of athersclerosis. Chemotaxis was determined by the method described in Stracke, et al., *J. Biol. Chem.* 264:21544 (1989). 10–20 μg/nL of soluble CD97 α was found to be chemotactic for A2058 melanoma cells, primary human coronary artery smooth muscle cells and human umbilical vein endothelial cells. Because smooth muscle cells are involved in the establishment and progression of atherosclerotic lesions, this data indicates soluble CD97 α from T-cells induces the migration to and maintenance of smooth muscle cells to atherosclerotic lesions, thus increasing the size of the lesion.

Example 10

Example 10 demonstrates that soluble CD97 α supports a neovascularization response in mice. This indicates soluble CD97 α is an angiogenic factor and a factor which contributes to an immune-mediated angiogenic response.

The extracellular domain of soluble CD97 α2 from transfected COS cells was incorporated into MATRIGEL® at a concentration of about 50 μg/mL (Passaniti, et al., *Lab. Invest.* 67:519 (1992)). The composition was injected into mice subcutaneously. Neovascularization was assessed by hostological examination.

Soluble CD97 α at 50 μg/mL together with basic fibroblast growth factor (bFGF) at a concentration of 50–150 ng/mL showed a very strong synergistic response compared to either bFGF or soluble CD97 α alone. Increased numbers of vessels as well as numerous large uncharacterized cells were observed after the injection of soluble CD97 α and bFGF.

Example 10

Example 10 teaches other species of CD97 α subunits.

From the sequences of the EGF repeat amino acid sequences given in FIG. 3, amino acid substitutions. It is expected that these substitutions would have minimal, if any, effects on the function of the CD97 α subunits.

These substitutions are made by site directed mutagenesis of the nucleic acid sequences that encode the specific subunit or of the CD97 proprotein sequence. Site directed mutagenesis is well known in the art and described in detail in Ausubel, et al., which is herein incorporated by reference.

From the desired amino acid sequence, synthetic oligonucleotides are designed to incorporate a mutation which results in a changed or additional amino acid at one end of an amplified fragment. Typically, the synthetic oligonucleotide is derived from another EGF repeat sequence. Following a PCR amplification of the fragments, they are blunt ended by treatment with Klenow fragment. The fragments are then ligated and subcloned into a vector to facilitate sequence analysis. Further ligation then is performed to create the entire coding sequence which incorporates the amino acid substitution or addition. The coding sequence is inserted into an expression vector and the CD97 α subunit is expressed.

The following is a table of substitutions that can be made to give CD97 α subunits with essentially complete activity. The amino acid positions correspond to amino acid positions of FIG. 1 and SEQ ID NO:6.

TABLE 2

| CD97 Subunit | Amino Acid Position | Substitution |
| --- | --- | --- |
| α1 | 23 | Serine to Valine |
|  | 73 | Lysine to Serine |
|  | 229 | Threonine to Asparagine |
|  | 41–42 | Addition of Tyrosine between Alanine and Cysteine |
| α2 | 39 | Alanine to Threonine |
|  | 83 | Tryptophan to Valine |
|  | 244 | Arginine to Isoleucine |
|  | 219–220 | Addition of Serine between Glutamine and Cysteine |
| α3 | 49 | Serine to Proline |
|  | 92 | Valine to Arginine |

TABLE 2-continued

| CD97 Subunit | Amino Acid Position | Substitution |
| --- | --- | --- |
|  | 252 | Lysine to Asparagine |
|  | 253–254 | Addition of a Lysine between Tyrosine and Valine |

It would be apparent to one of skill that other substitutions could be made to arrive at the proteins of the claimed invention.

All publications and patents mentioned in this specification are herein incorporated by reference into the specification to the same extent as if each individual publication or patent was specifically and individually indicated to be incorporated herein by reference.

What is claimed is:

1. An isolated soluble CD97 α subunit, wherein said soluble α subunit is selected from the group consisting of α1, α2, and α3, wherein:
   contact of endothelial cells with said soluble α subunit increases adherence of the endothelial cells;
   α3 has a molecular weight of about 45 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6;
   α2 has a molecular weight of about 50 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6; and,
   α1 has a molecular weight of about 55 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6.

2. The isolated protein of claim 1, wherein said α1 subunit further comprises an EGF-like repeat selected from the group consisting of SEQ ID NO:3, and SEQ ID NO:4, and wherein said α2 subunit further comprises EGF-like repeat SEQ ID NO:3.

3. The protein of claim 1, wherein the soluble CD97 α subunit is CD97 α2.

4. The protein of claim 1, wherein said protein is recombinantly produced.

5. An isolated soluble CD97 α subunit, wherein said subunit is an extracellular protein comprising at least 10 contiguous amino acids from the protein of SEQ ID NO:6, is increased at least five-fold upon maximal activation of a T-cell with a T-cell mitogen, and is immunologically cross-reactive to an antibody that is specifically reactive to the protein of SEQ ID NO:6.

6. A method for inhibiting angiogenesis associated with chronic inflammation in a mammal, comprising administering a therapeutically effective amount of an anti-CD97 α subunit antibody, wherein said CD97-subunit is selected from the group consisting of α1, α2 and α3 wherein:
   α3 has a molecular weight of about 45 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6;
   α2 has a molecular weight of about 50 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6;
   α1 has a molecular weight of about 55 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6.

7. The method of claim 6, wherein the therapeutically effective amount is administered topically or parenterally.

8. A method for inhibiting atherosclerosis in a mammal, comprising administering a therapeutically effective amount of an anti-CD97 α subunit antibody, wherein said CD97-subunit is selected from the group consisting of α1, α2 and α3 wherein:
   α3 has a molecular weight of about 45 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6;
   α2 has a molecular weight of about 50 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6;
   α1 has a molecular weight of about 55 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6.

9. A method of treating or inhibiting CD97 associated inflammation in a mammal, comprising administering a therapeutically effective amount of an anti-CD97 subunit antibody, and wherein said CD97-subunit is selected from the group consisting of α1, α2, and α3, wherein:
   α3 has a molecular weight of about 45 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6;
   α2 has a molecular weight of about 50 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6; and,
   α1 has a molecular weight of about 55 kDa in non-glycosylated form, has an EGF-like repeat selected from the group consisting of SEQ ID NO:1, SEQ ID NO:2, and SEQ ID NO:5, and is immunologically cross-reactive to an antibody that is specifically reactive to the protein of SEQ ID NO:6.

* * * * *

UNITED STATES PATENT AND TRADEMARK OFFICE
CERTIFICATE OF CORRECTION

PATENT NO. : 6,365,712 B1
DATED : April 2, 2002
INVENTOR(S) : Kathleen Kelly

It is certified that error appears in the above-identified patent and that said Letters Patent is hereby corrected as shown below:

Column 74,
Line 18, after "claim 6," insert -- 8, --.

Signed and Sealed this

Eighteenth Day of October, 2005

JON W. DUDAS
*Director of the United States Patent and Trademark Office*